US006784993B2

United States Patent
Opsal et al.

(10) Patent No.: US 6,784,993 B2
(45) Date of Patent: Aug. 31, 2004

(54) APPARATUS FOR OPTICAL MEASUREMENTS OF NITROGEN CONCENTRATION IN THIN FILMS

(75) Inventors: Jon Opsal, Livermore, CA (US); Youxian Wen, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 10/428,387

(22) Filed: May 2, 2003

(65) Prior Publication Data

US 2003/0206299 A1 Nov. 6, 2003

Related U.S. Application Data

(62) Division of application No. 09/864,981, filed on May 24, 2001, now Pat. No. 6,583,876.

(51) Int. Cl.[7] .................................................. G01J 4/00
(52) U.S. Cl. ....................................... 356/369; 356/432
(58) Field of Search .................................. 356/369, 432

(56) References Cited

U.S. PATENT DOCUMENTS

| | | | |
|---|---|---|---|
| 4,710,030 A | 12/1987 | Tauc et al. ................... 356/432 |
| 4,750,822 A | 6/1988 | Rosencwaig et al. ....... 356/445 |
| 5,298,970 A | 3/1994 | Takamatsu et al. .......... 356/349 |
| 5,608,526 A | 3/1997 | Piwonka-Corle et al. ... 356/369 |
| 5,798,837 A | 8/1998 | Aspnes et al. ............... 356/369 |
| 5,978,074 A | 11/1999 | Opsal et al. ................... 356/72 |
| 6,060,374 A | 5/2000 | Lin et al. ..................... 438/514 |
| 6,081,330 A | 6/2000 | Nelson et al. ............... 356/318 |
| 6,151,119 A | * 11/2000 | Campion et al. ........... 356/630 |
| 6,278,519 B1 | * 8/2001 | Rosencwaig et al. ....... 356/369 |
| 6,381,009 B1 | 4/2002 | McGahan ..................... 356/73 |

FOREIGN PATENT DOCUMENTS

| WO | WO 99/02970 | 1/1999 | .......... G01N/21/21 |
|---|---|---|---|
| WO | WO 00/20841 | 4/2000 | .......... G01N/21/17 |
| WO | WO 00/68656 | 11/2000 | .............. G01J/4/00 |

* cited by examiner

Primary Examiner—Diane I. Lee
Assistant Examiner—Lisa M. Caputo
(74) Attorney, Agent, or Firm—Stallman & Pollock LLP

(57) ABSTRACT

A system is disclosed for evaluating nitrogen levels in thin gate dielectric layers formed on semiconductor samples. In one embodiment, a tool is disclosed which includes both a narrow band ellipsometer and a broadband spectrometer for measuring the sample. The narrowband ellipsometer provides very accurate information about the thickness of the thin film layer while the broadband spectrometer contains information about the nitrogen levels. In another aspect of the subject invention, a thermal and/or plasma wave detection system is used to provide information about the nitrogen levels and nitration processes.

12 Claims, 13 Drawing Sheets

APPARATUS FOR OPTICAL MEASUREMENTS OF NITROGEN CONCENTRATION IN THIN FILMS

PRIORITY CLAIM

The present application is a divisional of and claims priority to U.S. patent application Ser. No. 09/864,981, filed May 24, 2001 now U.S. Pat. No. 6,583,876.

TECHNICAL FIELD

The subject invention relates to measurements of nitrogen content in thin films formed on semiconductor wafers. In particular, complimentary approaches are disclosed for monitoring nitrogen content which include thermal wave technology as well as spectroscopic and ellipsometric measurements.

BACKGROUND OF THE INVENTION

In the process of fabricating semiconductor devices, very thin films are used to form dielectric gates. Currently, silicon dioxide is the most common material used for the gate dielectric. With the push towards smaller devices, thinner gate dielectric layers are needed. Today, these layers are only 10 to 20 Angstroms thick. To obtain the necessary characteristics with these very thin layers, the industry is moving towards adding nitrogen to the silicon dioxide material.

The amount of nitrogen added to the silicon dioxide must be accurately controlled and therefore a precise method for measuring nitrogen concentration is required. Metrology efforts in the past have focused upon secondary ion mass spectrometry (SIMS) and X-Ray type measurements such as ESCA (Electron Spectroscopy for Chemical Analysis) or XPS (X-ray Photoemission Spectroscopy). Attempts have also been made to characterize nitrogen levels using either ellipsometry or spectroscopy.

It is believed that neither spectroscopy nor ellipsometry alone can provide sufficient information about nitrogen levels in a sample. Therefore, it would be desirable to develop one or more approaches for monitoring nitrogen levels that was fast, accurate and non-destructive.

SUMMARY OF THE INVENTION

In accordance with the subject invention, an approach has been developed which permits accurate evaluation of the nitrogen levels in an oxide layer. In this approach, two optical measurements of the semiconductor are made. The first measurement is based on a stable, narrowband ellipsometer. The information from the ellipsometer is useful for determining the thickness of the thin gate dielectric. This measurement is desired since an accurate determination of nitrogen levels based on an analysis of spectroscopic measurements also requires a very accurate knowledge of the layer thickness. A single wavelength, off-axis ellipsometer is one of the best tools for measuring the thickness of a very thin layer.

In accordance with the subject invention, a second measurement is made which is particularly sensitive to nitrogen concentration. This measurement is preferably a broadband multi-wavelength measurement. In initial experiments, it has been found that suitable information can be obtained from a reflectometry measurement, particularly concentrating in the UV wavelengths.

The measurements obtained from the narrowband ellipsometer and the reflectometer are used in combination to determine the thickness of the gate dielectric and the nitrogen concentration. More specifically, a theoretical model is set up which corresponds to the actual sample, including a substrate and at least the gate dielectric layer. The model includes various characteristics of the material, for example, thickness of the layer, index of refraction, and extinction coefficient. The model is typically seeded with initial parameters of the materials. Using the Fresnel equations, calculations are performed to determine expected measurement data if the modeled sample actually existed and was measured. This calculated data is then compared to the actual measured data. Differences between the calculated data and the actual measured data are then used to vary the expected characteristics of the sample of the model in an iterative process for determining the actual composition of the sample, including nitrogen levels.

The analysis of samples using a combination of a narrowband ellipsometer and another spectroscopic tool was described by assignee in PCT publication WO/9902970. This prior application described the benefits of using a narrowband ellipsometer to measure the thickness of a thin film or thin film stack and how that information can be combined with other measured data to characterize a multilayer structure. This disclosure herein is directed to extending that measurement concept for evaluating nitrogen levels in a dielectric layer.

In initial experiments, the subject approach provided a highly accurate analysis. This approach is also relatively mathematically intensive. In certain on-line production situations, it is desirable to have a fast testing procedure for monitoring nitrogen levels in real time.

It has been discovered that another metrology approach, a thermal and/or plasma wave analysis, can be used to provide a faster, precise measurement. In these systems, an intensity modulated pump laser beam is focused on the sample surface for periodically exciting the sample. In the case of a semiconductor, thermal and plasma waves are generated in the sample which spread out from the pump beam spot. These waves reflect and scatter off various features and interact with various regions within the sample in a way which alters the flow of heat and/or plasma from the pump beam spot. (For convenience, the term "thermal wave" will be used for the remainder of the specification and claims to represent the wave like phenomenon associated with periodic excitation and includes both thermal and plasma waves.)

The presence of the thermal waves has a direct effect on the reflectivity at the surface of the sample. Features and regions below the sample surface which alter the passage of the thermal waves will therefore alter the optical reflective patterns at the surface of the sample. By monitoring the changes in reflectivity of the sample at the surface, information about characteristics below the surface can be investigated.

In one monitoring approach, a second laser is provided for generating a probe beam of radiation. This probe beam is focused collinearly with the pump beam and reflects off the sample. A photodetector is provided for monitoring the power of the reflected probe beam. The photodetector generates an output signal which is proportional to the reflected power of the probe beam and is therefore indicative of the varying optical reflectivity of the sample surface.

The output signal from the photodetector is filtered to isolate the changes which are synchronous with the pump beam modulation frequency. In the preferred embodiment, a lock-in detector is used to monitor the magnitude and phase of the periodic reflectivity signal. This output signal is conventionally referred to as the modulated optical reflectivity (MOR) of the sample.

The assignee herein markets a product which operates in accordance with these principals under the trademark Therma-Probe. This device incorporates technology described in the following U.S. Pat. Nos. 4,634,290; 4,636,088, 4,854,710 and 5,074,669. The latter patents are incorporated herein by reference.

It is also known that thermal wave effects can be measured with other forms of probes. In particular, the periodic excitation produces periodic movement (deformation) at the surface of the sample which can be monitored. Such techniques include interferometry as well as the measurement of the periodic angular deflection of a probe beam. Information about such systems can be found in U.S. Pat. Nos. 4,521,118; 5,522,510; 5,298,970; and PCT publications, WO 00/20841 and 00/68656, all of which are incorporated herein by reference. Such systems for monitoring the variations of a probe beam are within the scope of the subject invention.

In all of the thermal wave systems, information about both the amplitude and phase of the periodic signal generated from monitoring changes in the probe beam can be extracted. It has been found that these signals, and particularly the amplitude signal, vary with nitrogen concentration and thus can be used to monitor the nitration process. In practice, it would be difficult to use the thermal wave signal to provide an accurate value for the nitrogen concentration. Such accurate measurements can, however, be obtained from the above described combination of ellipsometric and broadband detection system which generates far more data and permits a more specific analysis to be made. In contrast, the thermal wave amplitude signal provides only a single value. Nonetheless, the sensitivity of the thermal waves to nitrogen concentrations is very high such that a thermal wave detection system can be used to precisely monitor a semiconductor fabrication process.

In the preferred embodiment, the thermal wave measurement technique is calibrated using the ellipsometer/broadband technique. More specifically, one or more samples can be measured using the more information rich ellipsometer/broadband measurement as well as the thermal wave technique. As noted above, the ellipsometer/broadband technique can provide accurate information about nitrogen content of the sample. This information can be correlated with the thermal wave measurements so that the thermal wave measurements will also give an accurate result for that type of sample. Thermal wave measurements can be made in real time and therefore can provide a simple evaluation of process parameters.

The sensitivity of the thermal wave technique to nitrogen concentration is present only before the wafer is annealed. During the annealing process, where the wafer is typically heated, the physical structure changes so that the thermal wave signal no longer varies with respect to nitrogen concentration. For this reason, the thermal wave signal is also ideal as an indication of proper annealing. More specifically, if the wafer has been fully annealed, it will produce the same thermal wave signal no matter what the nitrogen level. If the wafer is measured after the annealing process, the extent of the which the wafer was successfully annealed can be evaluated.

Further objects and advantages of the subject invention will become apparent with the following detailed description, taken in conjunction with the drawings in which:

DETAILED DESCRIPTION OF THE PREFERRED EMBODIMENTS

In a first aspect of the subject invention, nitrogen concentrations in gate dielectrics can be accurately measured using a combination of the measurements obtained from a narrowband ellipsometer and at least one other measurement system, including for example, a broadband spectrophotometer. The metrology industry currently markets tools having more than one type of measurement module on a single platform. Assignees herein market such a device under the name Opti-Probe.

Figure 1:
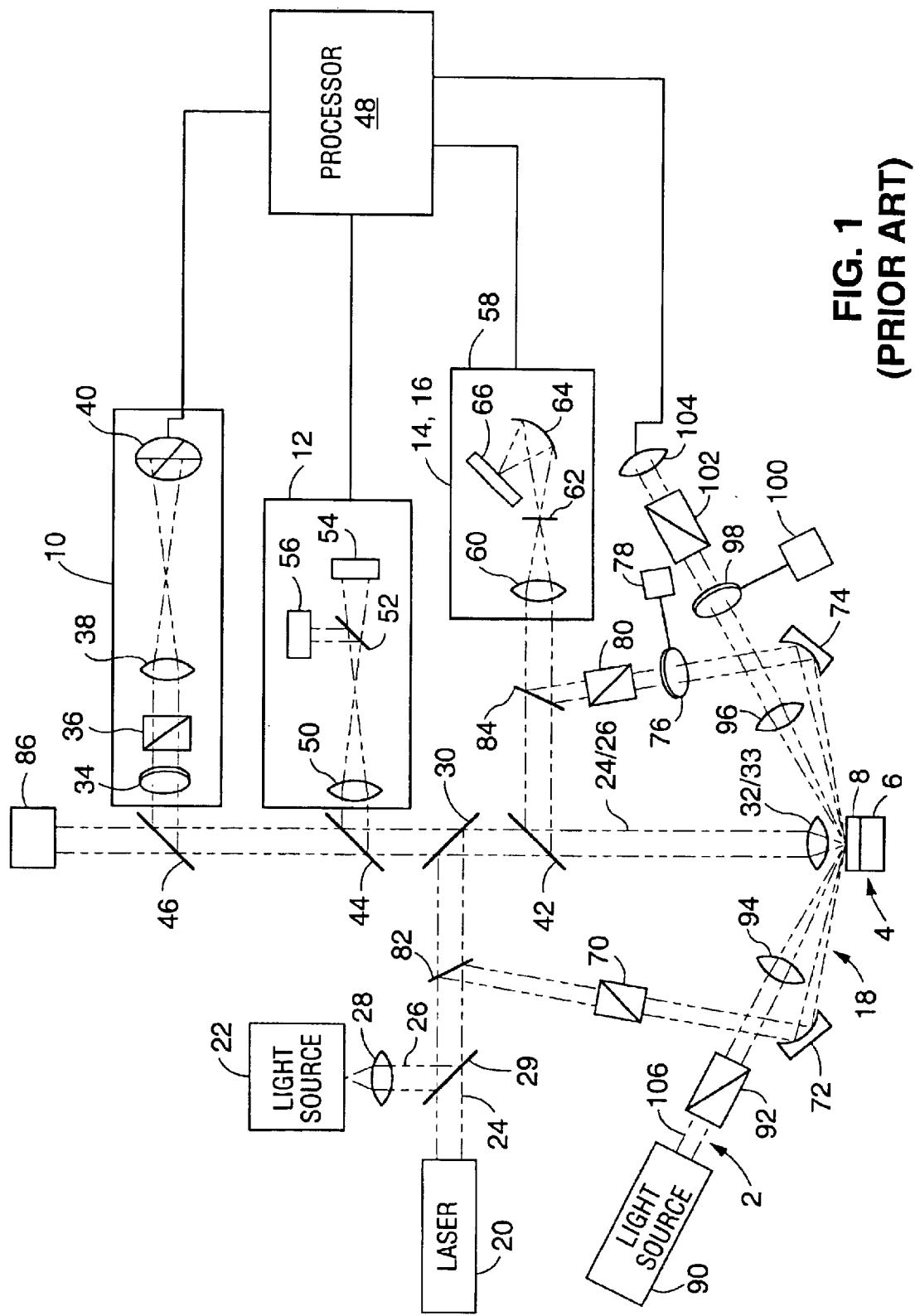
FIG. 1 is an illustration of an optical metrology device including a single wavelength ellipsometer in combination with additional measurement tools.

FIG. 1 is basic illustration of such a tool. This first aspect of the subject invention relates to using such a tool to produce measurements useful in analyzing nitrogen content in a gate dielectric. The device of FIG. 1 is described in greater detail in PCT application WO 99/02970, incorporated herein by reference. The elements of the device are described briefly herein.

The apparatus of FIG. 1 includes five different non-contact optical measurement devices as well as a narrow band, off-axis ellipsometer 2 for measuring a sample 4 including a substrate 6 and a thin gate dielectric 8. The composite optical measurement system 1 includes a Beam Profile Ellipsometer (BPE) 10, a Beam Profile Reflectometer (BPR) 12, a Broadband Reflective Spectrometer (BRS) 14, a Deep Ultra Violet Reflective Spectrometer (DUV) 16, and a Broadband Spectroscopic Ellipsometer (BSE) 18. These five optical measurement devices utilize as few as two optical sources: laser 20 and light source 22. Laser 20 generates a probe beam 24, and light source 22 generates probe beam 26 (which is collimated by lens 28 and directed along the same path as probe beam 24 by mirror 29). Laser 20 ideally is a solid state laser diode which emits a linearly polarized beam at 673 nm. Light source 22 is ideally a combination of two lamps, deuterium and tungsten, that produces a polychromatic beam that covers a spectrum of 190 nm to 820 nm. The probe beams 24/26 are reflected by mirror 30, and pass through mirror 42 to sample 4.

The probe beams 24/26 are focused onto the surface of the sample with a lens 32 or lens 33. In the preferred embodiment, two lenses 32/33 are mounted in a turret (not shown) and are alternatively movable into the path of probe beams 24/26. Lens 32 is a spherical, microscope objective lens with a high numerical aperture (on the order of 0.90 NA) to create a large spread of angles of incidence with respect to the sample surface, and to create a spot size of about one micron in diameter. Lens 33 is a reflective lens having a lower numerical aperture (on the order of 0.4 NA) and capable of focusing deep UV light to a spot size of about 10 to 15 microns.

Beam profile ellipsometry (BPE) is discussed in U.S. Pat. No. 5,181,080, issued Jan. 19, 1993, which is commonly owned by the present assignee and is incorporated herein by reference. BPE 10 includes a quarter wave plate 34, polarizer 36, lens 38 and a detector 40. In operation, linearly polarized probe beam 24 is focused onto sample 4 by lens 32. Light reflected from the sample surface passes up through lens 32, through mirrors 42, 30 and 44, and directed into BPE 10 by mirror 46. The position of the rays within the reflected probe beam correspond to specific angles of incidence with respect to the sample's surface. Quarter-wave plate 34 retards the phase of one of the polarization states of the beam by 90 degrees. Linear polarizer 36 causes the two polarization states of the beam to interfere with each other. For maximum signal, the axis of the polarizer 36 should be oriented at an angle of 45 degrees with respect to the fast and slow axis of the quarter-wave plate 34. Detector 40 is a quad-cell detector with four radially disposed quadrants that each intercept one quarter of the probe beam and generate a separate output signal proportional to the power of the portion of the probe beam striking that quadrant. The output signals from each quadrant are sent to a processor 48. As discussed in the U.S. Pat. No. 5,181,080 patent, by monitoring the change in the polarization state of the beam, ellipsometric information, such as $\psi$ and $\Delta$, can be determined. To determine this information, the processor 48 takes the difference between the sums of the output signals of diametrically opposed quadrants, a value which varies linearly with film thickness for very thin films.

Beam profile reflectometry (BPR) is discussed in U.S. Pat. No. 4,999,014, issued on Mar. 12, 1991, which is commonly owned by the present assignee and is incorporated herein by reference. BPR 12 includes a lens 50, beam splitter 52 and two linear detector arrays 54 and 56 to measure the reflectance of the sample. In operation, linearly polarized probe beam 24 is focused onto sample 4 by lens 32, with various rays within the beam striking the sample surface at a range of angles of incidence. Light reflected from the sample surface passes up through lens 32, through mirrors 42 and 30, and directed into BPR 12 by mirror 44. The position of the rays within the reflected probe beam correspond to specific angles of incidence with respect to the sample's surface. Lens 50 spatially spreads the beam two-dimensionally. Beam splitter 52 separates the S and P components of the beam, and detector arrays 54 and 56 are oriented orthogonal to each other to isolate information about S and P polarized light. The higher angles of incidence rays will fall closer to the opposed ends of the arrays. The output from each element in the diode arrays will correspond to different angles of incidence. Detector arrays 54/56 measure the intensity across the reflected probe beam as a function of the angle of incidence with respect to the sample surface. The processor 48 receives the output of the detector arrays 54/56.

Broadband reflective spectrometer (BRS) 14 simultaneously probes the sample 4 with multiple wavelengths of light. BRS 14 uses lens 32 and includes a broadband spectrometer 58 which can be of any type commonly known and used in the prior art. The spectrometer 58 shown in FIG. 1 includes a lens 60, aperture 62, dispersive element 64 and detector array 66. During operation, probe beam 26 from light source 22 is focused onto sample 4 by lens 32. Light reflected from the surface of the sample passes up through lens 32, and is directed by mirror 42 (through mirror 84) to spectrometer 58. The lens 60 focuses the probe beam through aperture 62, which defines a spot in the field of view on the sample surface to analyze. Dispersive element 64, such as a diffraction grating, prism or holographic plate, angularly disperses the beam as a function of wavelength to individual detector elements contained in the detector array 66. The different detector elements measure the optical intensities (magnitude) of the different wavelengths of light contained in the probe beam, preferably simultaneously. Alternately, detector 66 can be a CCD camera, or a photo-multiplier with suitably dispersive or otherwise wavelength selective optics. It should be noted that a monochrometer could be used to measure the different wavelengths serially (one wavelength at a time) using a single detector element. Further, dispersive element 64 can also be configured to disperse the light as a function of wavelength in one direction, and as a function of the angle of incidence with respect to the sample surface in an orthogonal direction, so that simultaneous measurements as a function of both wavelength and angle of incidence are possible. Processor 48 processes the intensity information measured by the detector array 66.

Deep ultra violet reflective spectrometry (DUV) simultaneously probes the sample with multiple wavelengths of ultra-violet light. DUV 16 uses the same spectrometer 58 to analyze probe beam 26 as BRS 14, except that DUV 16 uses the reflective lens 33 instead of focusing lens 32. To operate DUV 16, the turret containing lenses 32/33 is rotated so that reflective lens 33 is aligned in probe beam 26. The reflective lens 33 is necessary because solid objective lenses cannot sufficiently focus the UV light onto the sample.

Broadband spectroscopic ellipsometry (BSE) is discussed in U.S. Pat. No. 5,877,859, issued Mar. 2, 1999, which is commonly owned by the present assignee and is incorporated herein by reference. BSE (18) includes a polarizer 70, focusing mirror 72, collimating mirror 74, rotating compensator 76, and analyzer 80. In operation, mirror 82 directs at least part of probe beam 26 to polarizer 70, which creates a known polarization state for the probe beam, preferably a linear polarization. Mirror 72 focuses the beam onto the sample surface at an oblique angle, ideally on the order of 70 degrees to the normal of the sample surface. Based upon well-known ellipsometric principles, the reflected beam will generally have a mixed linear and circular polarization state after interacting with the sample, based upon the composition and thickness of the sample's film 8 and substrate 6. The reflected beam is collimated by mirror 74, which directs the beam to the rotating compensator 76. Compensator 76 introduces a relative phase delay δ (phase retardation) between a pair of mutually orthogonal polarized optical beam components. Compensator 76 is rotated at an angular velocity ω about an axis substantially parallel to the propagation direction of the beam, preferably by an electric motor 78. Analyzer 80, preferably another linear polarizer, mixes the polarization states incident on it. By measuring the light transmitted by analyzer 80, the polarization state of the reflected probe beam can be determined. Mirror 84 directs the beam to spectrometer 58, which simultaneously measures the intensities of the different wavelengths of light in the reflected probe beam that pass through the compensator/analyzer combination. Processor 48 receives the output of the detector 66, and processes the intensity information measured by the detector 66 as a function of wavelength and as a function of the azimuth (rotational) angle of the compensator 76 about its axis of rotation, to solve the ellipsometric values ψ and Δ as described in U.S. Pat. No. 5,877,859. Detector/camera 86 is positioned above mirror 46, and can be used to view reflected beams off of the sample 4 for alignment and focus purposes.

The subject device further includes a narrow-band ellipsometer 2. Ellipsometer 2 includes a light source 90 that produces a quasi-monochromatic probe beam 106 having a known stable wavelength and stable intensity. Preferably, this result is achieved passively, where light source 90 generates a very stable output wavelength which does not vary over time (i.e. varies less than 1%). Examples of passively stable light sources are a helium-neon laser, or other gas discharge laser systems.

The beam 106 interacts with polarizer 92 to create a known polarization state. In the preferred embodiment, polarizer 92 is a linear polarizer made from a quartz Rochon prism, but in general the polarization does not necessarily have to be linear, nor even complete. Polarizer 92 can also be made from calcite. The azimuth angle of polarizer 92 is oriented so that the plane of the electric vector associated with the linearly polarized beam exiting from the polarizer 92 is at a known angle with respect to the plane of incidence (defined by the propagation direction of the beam 106 and the normal to the surface of sample 4). The azimuth angle is preferably selected to be on the order of 30 degrees because the sensitivity is optimized when the reflected intensities of the P and S polarized components are approximately balanced. It should be noted that polarizer 92 can be omitted if the light source 90 emits light with the desired known polarization state.

The beam 106 is focused onto the sample 4 by lens 94 at an oblique angle. The beam 106 is ideally incident on sample 4 at an angle on the order of 70 degrees to the normal of the sample surface because sensitivity to sample properties is maximized in the vicinity of the Brewster or pseudo-Brewster angle of a material. Based upon well known ellipsometric principles, the reflected beam will generally have a mixed linear and circular polarization state after interacting with the sample, as compared to the linear polarization state of the incoming beam. Lens 96 collimates beam 106 after its reflection off of the sample 4.

The beam 106 then passes through the rotating compensator (retarder) 98, which introduces a relative phase delay δ (phase retardation) between a pair of mutually orthogonal polarized optical beam components. The amount of phase retardation is a function of the wavelength, the dispersion characteristics of the material used to form the compensator, and the thickness of the compensator. Compensator 98 is rotated at an angular velocity ω about an axis substantially parallel to the propagation direction of beam 106, preferably by an electric motor 100. Compensator 98 can be any conventional wave-plate compensator, for example those made of crystal quartz. The thickness and material of the compensator 98 are selected such that a desired phase retardation of the beam is induced. In the preferred embodiment, compensator 98 is a bi-plate compensator constructed of two parallel plates of anisotropic (usually birefringent) material, such as quartz crystals of opposite handedness, where the fast axes of the two plates are perpendicular to each other and the thicknesses are nearly equal, differing only by enough to realize a net first-order retardation for the wavelength produced by the light source 90.

Beam 106 then interacts with analyzer 102, which serves to mix the polarization states incident on it. In this embodiment, analyzer 102 is another linear polarizer, preferably oriented at an azimuth angle of 45 degrees relative to the plane of incidence. However, any optical device that serves to appropriately mix the incoming polarization states can be used as an analyzer. The analyzer 102 is preferably a quartz Rochon or Wollaston prism. The rotating compensator 98 changes the polarization state of the beam as it rotates.

It should be noted that the compensator 98 can be located either between the sample 4 and the analyzer 102 (as shown in FIG. 1), or between the sample 4 and the polarizer 92. It should also be noted that polarizer 70, lenses 94/96, compensator 98 and polarizer 102 are all optimized in their construction for the specific wavelength of light produced by light source 90, which maximizes the accuracy of ellipsometer 2.

Beam 106 then enters detector 104, which measures the intensity of the beam passing through the compensator/analyzer combination. The processor 48 processes the intensity information measured by the detector 104 to determine the polarization state of the light after interacting with the analyzer, and therefore the ellipsometric parameters of the sample. This information processing includes measuring beam intensity as a function of the azimuth (rotational) angle of the compensator about its axis of rotation. This measurement of intensity as a function of compensator rotational angle is effectively a measurement of the intensity of beam 106 as a function of time, since the compensator angular velocity is usually known and a constant.

The scope of the present invention includes any ellipsometer configuration in conjunction with the light source 90 (having a stable, narrow-band wavelength) that measures the polarization state of the beam after interaction with the sample. For example, another ellipsometric configuration is to rotate polarizer 92 or analyzer 100 with motor 100, instead of rotating the compensator 98.

In addition, null ellipsometry, which uses the same elements as ellipsometer 2 of FIG. 1, can be used. The ellipsometric information is derived by aligning the azimuthal angles of these elements until a null or minimum level intensity is measured by the detector 104. In the preferred null ellipsometry embodiment, polarizers 92 and 102 are linear polarizers, and compensator 98 is a quarter-wave plate. Compensator 98 is aligned so that its fast axis is at an azimuthal angle of 45 degrees relative to the plane of incidence of the sample 4. Polarizer 92 has a transmission axis that forms an azimuthal angle relative to the plane of incidence, and polarizer 102 has a transmission axis that forms an azimuthal angle relative to the plane of incidence. Polarizers 92 and 102 are rotated about beam 106 such that the light is completely extinguished (minimized) by the analyzer 102. In general, there are two polarizer 92/102 orientations that satisfy this condition and extinguish the light. Null ellipsometry is very accurate because the results depend entirely on the measurement of mechanical angles, and are independent of intensity.

It is also conceivable to omit compensator 98 from ellipsometer 2, and use motor 100 to rotate polarizer 92 or analyzer 102. Either the polarizer 92 or the analyzer 102 is rotated so that the detector signal can be used to accurately measure the linear polarization component of the reflected beam. Then, the circularly polarized component is inferred by assuming that the beam is totally polarized, and what is not linearly polarized must be circularly polarized.

In accordance with the subject invention, nitrogen content in the thin film layer 8 formed on sample 4 can be determined by taking at least two measurements. One of the two measurements is obtained from the ellipsometer 2. Such a stable single wavelength ellipsometer can provide highly accurate information about layer thickness.

The data obtained from the ellipsometer 2 can be combined with data taken from one or more of the other measurement devices. In initial experiments, it has been found that good results can be obtained from the spectrometer measurements, particularly at the UV wavelengths. However, it is within the scope of the subject invention to use any one or more of the other measurement devices discussed above.

Once the measurements are taken, they are supplied to a processor for determining the nitrogen content of the film. The reflectivity measurements are preferably normalized to a known reference material as a means to remove the effects of optical artifacts in the measurement system. In this application, the data can be improved by using a reference sample that comes from the process immediately prior to nitridation. Once the data is normalized, the processor uses a recipe which includes a model of the sample including the substrate and at least the gate dielectric layer. The model includes various characteristics of the material, for example, thickness of the layer, index of refraction, and extinction coefficient. The model is typically seeded with initial parameters of the materials. Using the Fresnel equations, calculations are performed to determine expected measurement data if the modeled sample actually existed and was measured. This calculated data is then compared to the actual measured data. Differences between the calculated data and the actual measured data are then used to vary the expected characteristics of the sample of the model in an iterative process for determining the actual composition of the sample, including nitrogen levels.

The model is weighted such that the data from the ellipsometer 2 constrains the solutions for layer thickness while the data from the broad band measurements constrains the solution for nitrogen content.

EXPERIMENTAL EXAMPLES

Introduction

Using an Opti-Probe and combining the ellipsometer 2 (AE) and broadband (BB) technologies, over fifty 8" thin oxide wafers which were nitrided under either remote plasma nitridation (RPN) or decouple plasma nitridation (DPN) process were evaluated. In this study, a three-parameter $\{t, f_{SiO2}, f_{Si3N4}\}$ recipe has been developed. The recipe employs the AE for measuring the oxide thickness with the best repeatability, together with the broadband spectrometer (S) to measure the nitrogen (N) concentration via its effect on the DUV properties of the film.

Results show a clear trend from 0% to 50% in $fSi_3N_4$, or from 0% to 40% in $f_N$, among the wafers. A comparison of Opti-Probe to other technologies, i.e., secondary ion mass spectrometer (SIMS), nuclear reaction analysis (NRA) and variable angle spectral ellipsometer (VASE) is discussed below. A correlation with SIMS results is also presented. The effect of adsorbed environmental film on the surface is discussed, which can be minimized by implementing desorbing technology of the type described in copending U.S. application Ser. No. 09/499,478, filed Feb. 7, 2000. A repeatability of 1.5% on N concentration was obtained from a three-day measurement run involving fifteen load/measure/unload cycles.

Beside film thickness and nitrogen content, the interface states between the nitrided oxide film and its Si-substrate is also critical to electronic performance of gate devices. Studies on a assignee's thermal wave metrology device (Therma-Probe) show that variation at the interface of the Si-substrate induced by changes in process parameters can be detected with an extremely high sensitivity.

This study demonstrates the capability of the Opti-Probe and Therma-Probe to monitor thickness, nitrogen concentration in thin nitrided oxide films and its interface states.

A total of eleven 8" RPN samples were used to verify this method. The samples as well as the measurements performed on each wafer are listed in table 1 below:

TABLE 1

| | RPN wafers | |
|---|---|---|
| Box | Slots | Measurement |
| 1 | 2, 4, 6, 8, 10, 12, 14, 16, 18, 20, 22 | $\{t, f_{SiO2}, f_{Si3N4}\}$ |

A total of five 1" square PRN samples were used to verify this method. The samples as well as the measurements performed on each wafer are listed in table 2 below:

TABLE 2

| | RPN wafers | |
|---|---|---|
| Box | Slots | Measurement |
| 1 | 11, 13, 15, 17, 19 | $\{t, f_{SiO2}, f_{Si3N4}\}$ |

A total of forty-five 8" DPN samples with various nitrogen atomic contents were used to verify process independency and repeatability studies. The samples as well as the measurements performed on each wafer are listed in table 3 below:

TABLE 3

| | DPN Wafers | |
|---|---|---|
| Box | Slots | Measurement |
| 1 | 1, 2, 4–7, 10–16, 18, 19, 22–24 | $\{t, f_{SiO2}, f_{Si3N4}\}$ |
| 2 | 5–8 | $\{t, f_{SiO2}, f_{Si3N4}\}$ |
| 3 | 1–20 | $\{t, f_{SiO2}, f_{Si3N4}\}$ |
| 4 | 1–5 | $\{t, f_{SiO2}, f_{Si3N4}\}$ |

An Opti-Probe was used to monitor the DPN process on total of 268 8" DPN samples. The samples as well as the measurements performed on each wafer are listed in table 4 below:

TABLE 4

| DPN Wafers monitored on an Opti-Probe and a Therma-Probe | | | |
|---|---|---|---|
| Box | Description | # of sample | Measurement |
| 1 | Customer DPN Marathon | 18 + 7ref | $\{t, f_{SiO2}, f_{Si3N4}\}$ |
| 2–17 | DPN Hardware Test | 243 | $\{t, f_{SiO2}, f_{Si3N4}\}$ |

Measurements Performed

1. Single point measurements.
2. 15-time load/unload repeatability: A 15-time repeatability value for each wafer is defined as the standard deviation of 15-time load/unload measurements for a period of three days.
3. Three points 1 mm horizontal linescan measurements.
4. 21-point linescan measurements: 21-point linescan measurements with 6-mm edge exclusion.
5. 21-point linescan measurements with desorber: Prior to each 21-point linescan measurement with 6-mm edge exclusion, a standard desorber was used to desorb the wafers at 400° for 300 seconds and 15 second for cooling.
6. 21-point linescan measurements on a Therma-Probe: 21-point linescan measurements with 6-mm edge exclusion were performed on some wafers on a Therma-Probe.

Results and Discussion

Methodology: Development and Verification on RPN Wafers

In order to monitor the nitrogen atomic content, an effective medium (EMA) dispersion model for the nitrided oxide was developed.

Figure 2A:
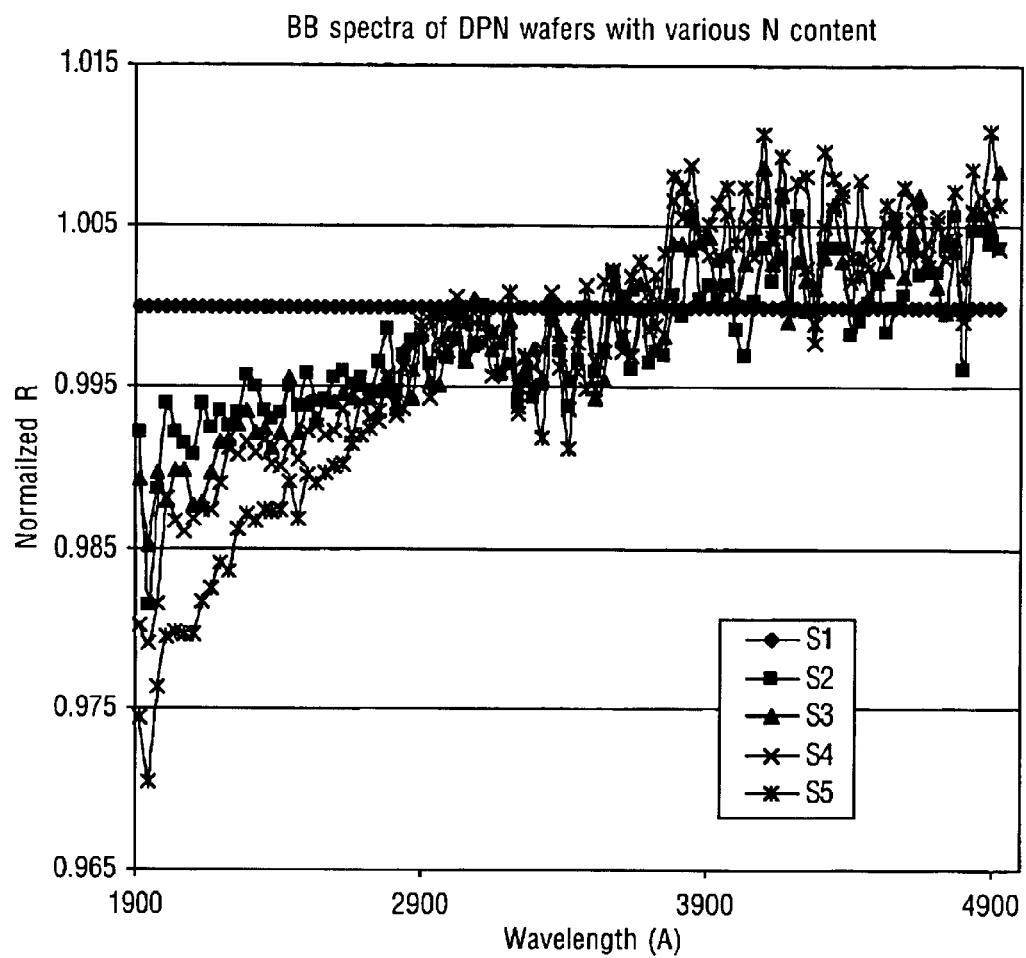
FIG. 2a is a graph showing broadband spectra of DPN wafers with various nitrogen content.
Figure 2B:
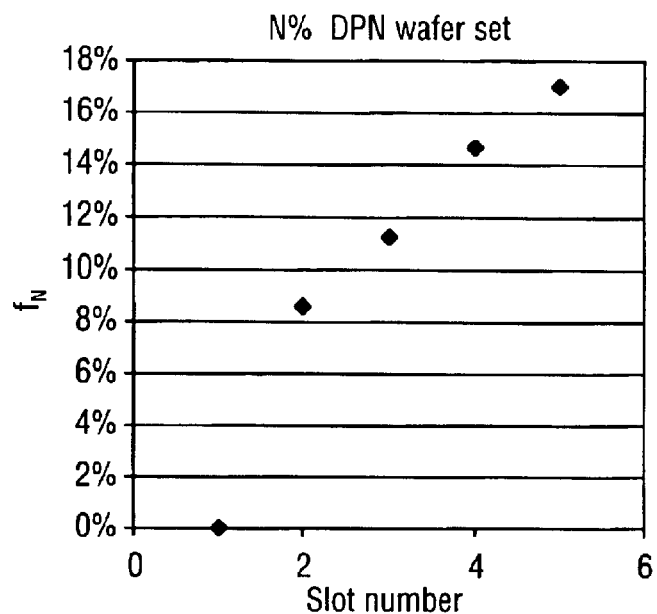
FIG. 2b is a graph showing the percentage of nitrogen concentration in a DPN wafer set.

Since there is a slight spectral change in deep UV wavelength region due to N contents in each sample as illustrated in FIGS. 2a and 2b. i) the sample with zero N content as in the slot 1 has to be selected as a new reference in the data analysis; ii) a narrow spectral range from 190 nm to 250 nm of BB is chosen in the final recipe. The thickness and both fractions of two components ($SiO_2$ and $Si_3N_4$) are floating in the final fit. The $\{t, f_{SiO2}, f_{Si3N4}\}$ recipe has been applied for all thin nitrided oxide samples in this study using a combination of AE and BB technologies of Opti-Probe. As used herein the "BB" or broadband technologies is meant to include the Broadband Reflective Spectrometer (BRS), the Deep Ultra Violet Reflective Spectrometer (DUV), and the Broadband Spectroscopic Ellipsometer (BSE). In the actual experiments, the most significant data was obtained from the DUV measurements in the range of 190 to 250 nm.

In table 5, a comparison of Opti-Probe results to SIMS data is given. In the table, N contents of each wafer pair were assumed to be identical to each other. The atomic content of nitrogen atom is defined below:

$$f_N = N_N/(N_N+N_O)*100\% = 4/3 f_{Si3N4}/(4/3 f_{Si3N4}+2*f_{SiO2})*100\%$$

Here, $N_N$ and $N_O$ is the total number of nitrogen and oxygen atoms; $f_{Si3N4}$ and $f_{SiO2}$ is the fraction of silicon nitride and silicon oxide, respectively.

TABLE 5

Summary of Opti-Probe results on eleven RPN wafers

| Slot# | t | $f_{SiO2}$ | $f_{Si3N4}$ | N %_OP | N %_SIMS | Expect % |
|---|---|---|---|---|---|---|
| 1 | | | | | | 8.5 |
| 2 | 25.18 | 0.86 | 0.14 | 9.1 | | 8.5 |
| 3 | | | | | 5 | 8.0 |
| 4 | 24.62 | 0.90 | 0.10 | 6.4 | 5 | 8.0 |
| 5 | | | | | | 12.5 |
| 6 | 25.33 | 0.89 | 0.11 | 7.1 | | 12.5 |
| 7 | | | | | 8 | 12.0 |
| 8 | 24.87 | 0.90 | 0.10 | 6.5 | 8 | 12.0 |
| 9 | | | | | 11 | 16.5 |
| 10 | 25.36 | 0.85 | 0.15 | 9.7 | 11 | 16.5 |
| 11 | | | | | 10 | 16.0 |
| 12 | 24.58 | 0.88 | 0.12 | 7.9 | 10 | 16.0 |
| 13 | | | | | 14 | 18.5 |
| 14 | 25.25 | 0.80 | 0.20 | 12.3 | 14 | 18.5 |
| 15 | | | | | 13 | 18.0 |
| 16 | 24.39 | 0.81 | 0.19 | 12.0 | 13 | 18.0 |
| 19 | | | | | | 20.5 |
| 18 | 25.23 | 0.79 | 0.21 | 12.9 | | 20.5 |
| 19 | | | | | 15 | 20.0 |
| 20 | 24.17 | 0.80 | 0.20 | 12.6 | 15 | 20.0 |
| 21 | | | | | | 0.0 |
| 22 | 24.17 | 1.00 | 0.00 | 0.0 | 0 | 0.0 |

Figure 3:
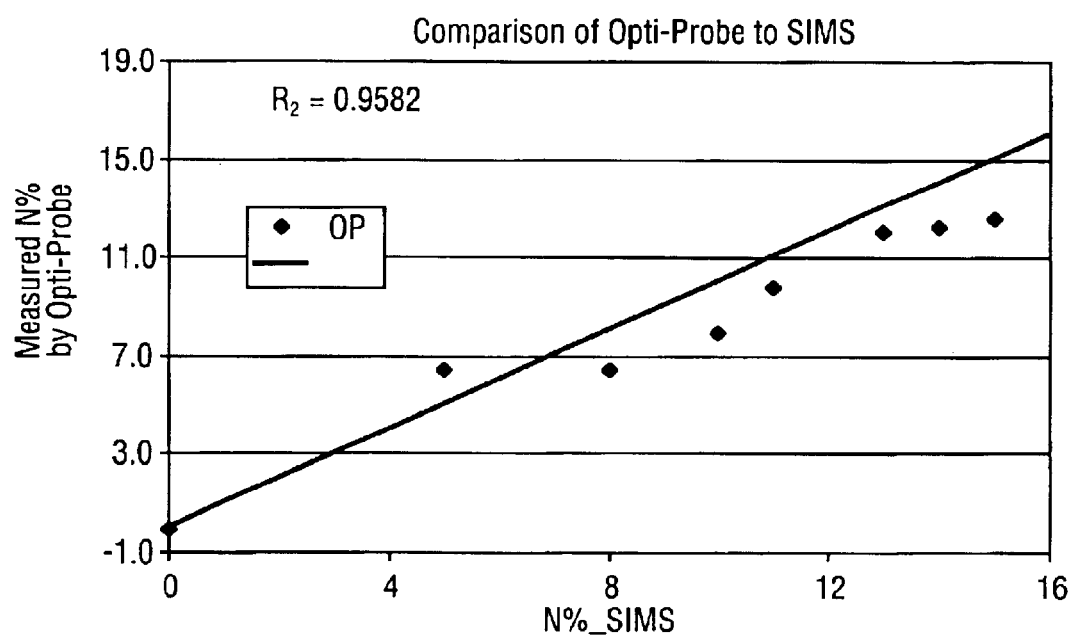
FIG. 3 is a graph comparing optical measurements to a SIMS measurement.

FIG. 3 presents a good correlation between Opti-Probe and SIMS. The solid line indicates the perfect correlation. The SIMS data was obtained from an identical wafer set under the same process condition per each wafer pair.

Comparison of Opti-Probe to Other Independent Technologies: Nuclear Reaction Analysis (NRA) and Variable Angle Spectral Ellipsometry (VASE).

Additional to the SIMS comparison in the previous section, the same recipe was applied on the five 1" square samples with higher Nitrogen contents. In table 6, a comparison among Opti-Probe, NRA (nuclear reaction analysis) and a commercial VASE has been presented. For samples with less than 25% Nitrogen content, the previous AE/BB approach show a good agreement to VASE. Both OP and VASE results are slightly lower than the NRA on moderate high concentrated sample, which could be due to accumulation of environmental film on samples.

TABLE 6

A comparison among three independent technologies on the same samples

| | OP (AE/BB(190–250 nm)) | | | | | | NRA | | VASE | |
|---|---|---|---|---|---|---|---|---|---|---|
| Slot | t | σt | $f_{Si3N4}$ | σ_$f_{Si3N4}$ | $f_N$ | σ_$f_N$ | $f_N$ | σ_$f_N$ | $f_N$ | σ_$f_N$ |
| 11 | 28.46 | 0.78 | 2.5% | 1.2% | 1.6% | 0.8% | 1.2% | 0.2% | 3.0% | 2.8% |
| 13 | 24.30 | 0.12 | 8.9% | 1.3% | 6.1% | 0.8% | 4.4% | 0.6% | 5.5% | 3.4% |
| 15 | 21.98 | 0.26 | 9.8% | 1.3% | 6.7% | 0.9% | 7.4% | 1.0% | 7.0% | 3.6% |
| 17 | 24.83 | 0.19 | 28.8% | 1.3% | 21.2% | 0.9% | 32.0% | 4.1% | 22.6% | 3.0% |
| 19 | 39.57 | 0.33 | 34.4% | 0.9% | 25.9% | 0.6% | 58.5% | 7.1% | 46.4% | 5.3% |

TABLE 6-continued

A comparison among three independent technologies on the same samples

| | OP (AE/BB(190–210 nm)) | | | | | NRA | | VASE | |
|---|---|---|---|---|---|---|---|---|---|
| Slot | t | σt | $f_{Si3N4}$ | $\sigma\_f_{Si3N4}$ | $f_N$ | $\sigma\_f_N$ | $f_N$ | $\sigma\_f_N$ | $f_N$ | $\sigma\_f_N$ |
| 11 | 28.67 | 0.57 | 3.0% | 2.6% | 2.0% | 1.8% | 1.2% | 0.2% | 3.0% | 2.8% |
| 13 | 23.23 | 0.09 | 10.0% | 1.2% | 6.9% | 0.8% | 4.4% | 0.6% | 5.5% | 3.4% |
| 15 | 21.41 | 0.14 | 10.3% | 1.1% | 7.1% | 0.8% | 7.4% | 1.0% | 7.0% | 3.6% |
| 17 | 21.75 | 0.11 | 33.7% | 1.2% | 25.3% | 0.8% | 32.0% | 4.1% | 22.6% | 3.0% |
| 19 | 27.51 | 0.10 | 53.4% | 0.8% | 43.3% | 0.5% | 58.5% | 7.1% | 46.4% | 5.3% |

The adsorption of environmental film will be discussed below. For higher concentrated sample, due to non-linearity of the sample, a modified EMA recipe using narrower spectral range of BB was developed to determine the nitrogen content, which shows a better correlation among these three technologies.

Repeatability Study

In order to monitor the nitrogen atomic content as well as robustness of the OP approach, the same effective medium (EMA) dispersion model using AE and BB(190–250 nm) for the remote plasma nitridation (RPN) wafers was applied to determine the nitrogen content of decouple plasma nitridation (DPN) wafers. The samples with zero N content as in the slot 24 in table 7 was selected as a new reference in the data analysis.

Table 7 provides 15-time load/unload results at each wafer center, which shows clear trends in nitrogen atomic contents within each group.

Figure 4:
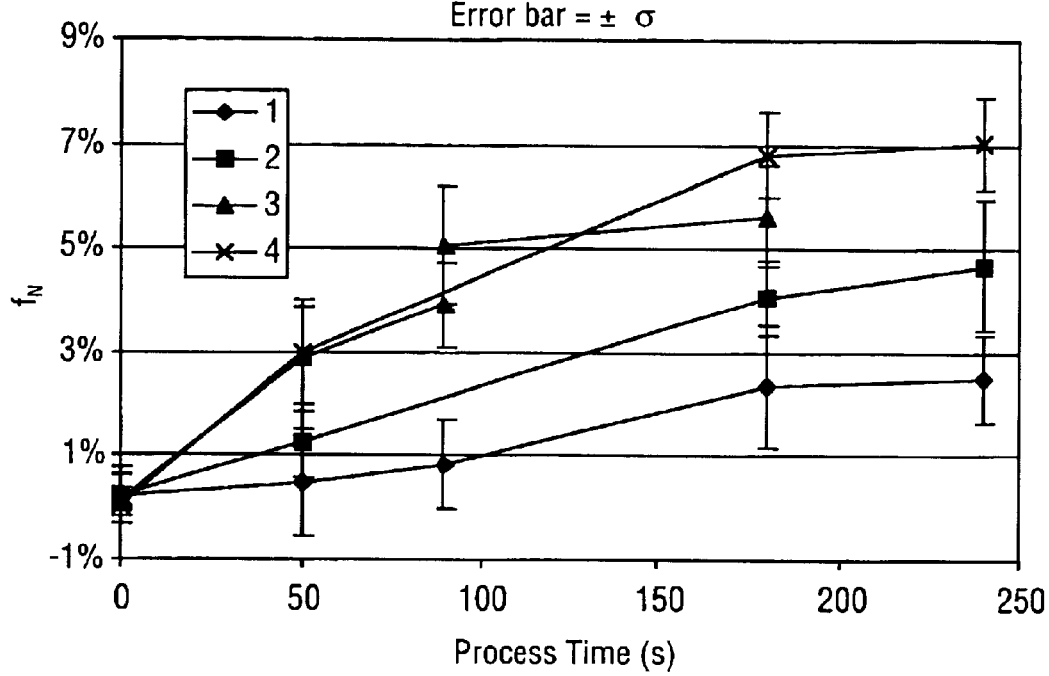
FIG. 4 is a graph illustrating optical measurements of various wafers.
Figure 5:
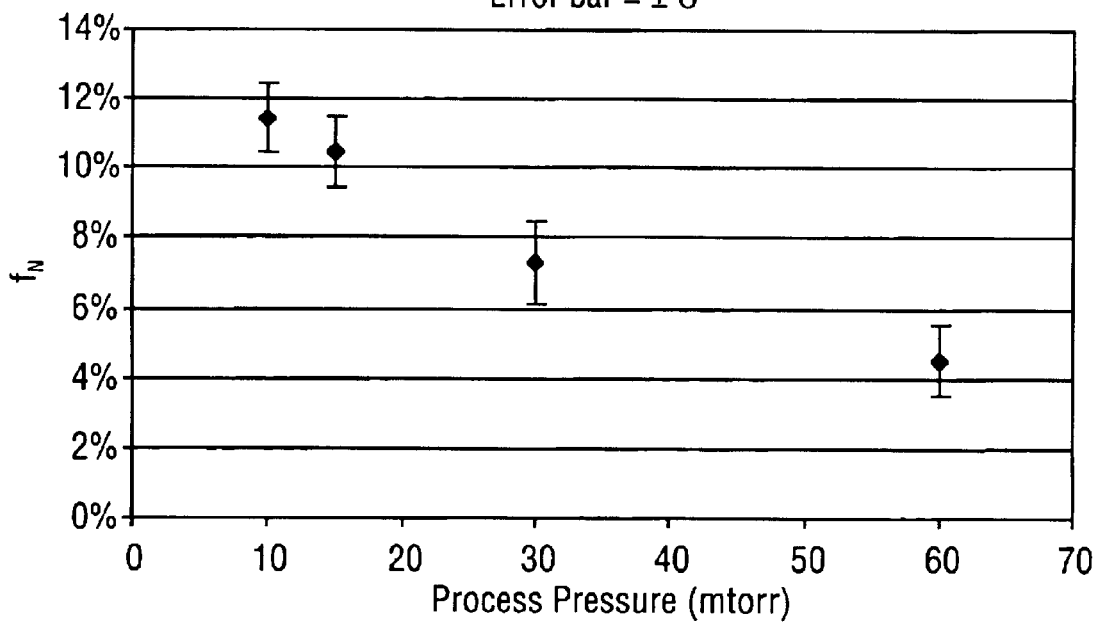
FIG. 5 is a graph illustrating optical measurements of various wafers.
Figure 6:
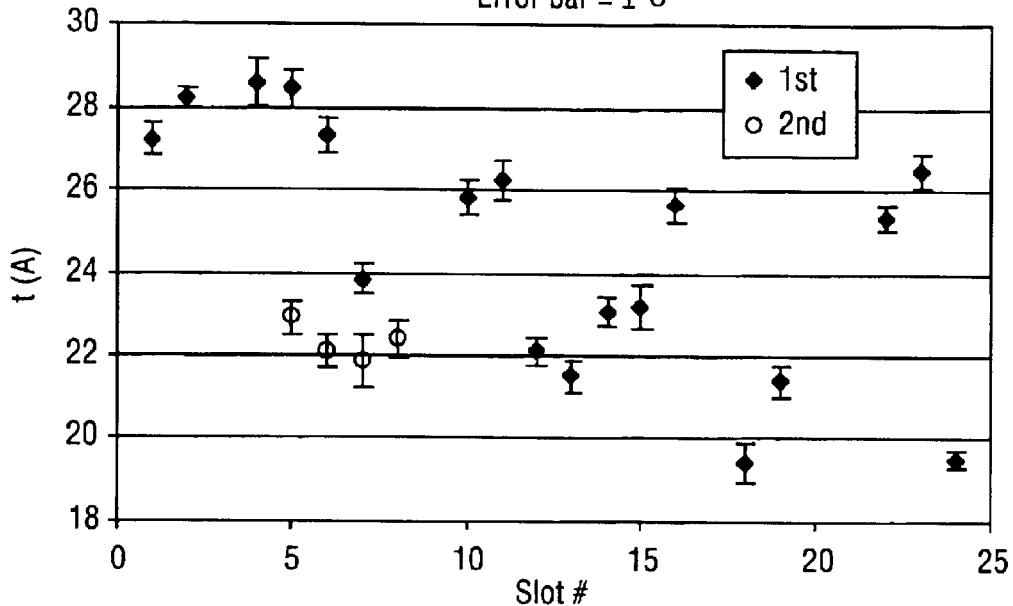
FIG. 6 is a graph illustrating optical measurements of various wafers.

Results of the 15-time load/unload repeatability of all wafers are illustrated in FIGS. 4–6. A process dependency of nitrogen contents among these wafers has been clearly presented in both FIGS. 4 and 5, which also demonstrates the capability of the Opti-Probe to determine nitrogen contents in thin nitrided oxide films

TABLE 7

Opti-Probe results for atomic fraction & thickness
Measurement sequence was a 15-time load/unload run over three days for each wafer:

| Slot | Mean-$f_{Si3N4}$ | $\sigma\_f_{Si3N4}$ | Mean-$f_N$ | $\sigma\_f_N$ | Mean-t | σ_t | Process Time (s) |
|---|---|---|---|---|---|---|---|
| 1 | 0.7% | 1.5% | 0.5% | 1.0% | 27.22 | 0.39 | 50 |
| 2 | 1.3% | 1.3% | 0.8% | 0.9% | 28.23 | 0.24 | 90 |
| 4 | 3.5% | 1.7% | 2.4% | 1.2% | 28.60 | 0.55 | 180 |
| 5 | 3.7% | 1.2% | 2.5% | 0.8% | 28.45 | 0.45 | 240 |
| 6 | 0.3% | 0.6% | 0.2% | 0.4% | 27.35 | 0.41 | 0 |
| 7 | 1.9% | 1.1% | 1.3% | 0.7% | 23.86 | 0.35 | 50 |
| 10 | 6.0% | 1.0% | 4.1% | 0.7% | 25.84 | 0.40 | 180 |
| 11 | 6.8% | 1.8% | 4.7% | 1.3% | 26.25 | 0.50 | 240 |
| 12 | 0.4% | 0.8% | 0.2% | 0.6% | 22.09 | 0.33 | 0 |
| 13 | 4.2% | 1.5% | 2.9% | 1.0% | 21.50 | 0.39 | 50 |
| 14 | 5.8% | 1.2% | 3.9% | 0.8% | 23.04 | 0.35 | 90 |
| 15 | 7.4% | 1.6% | 5.0% | 1.1% | 23.18 | 0.52 | 90 |
| 16 | 8.2% | 1.4% | 5.6% | 1.0% | 25.67 | 0.41 | 180 |
| 18 | 0.2% | 0.3% | 0.2% | 0.2% | 19.45 | 0.47 | 0 |
| 19 | 4.4% | 1.5% | 3.0% | 1.0% | 21.37 | 0.38 | 50 |
| 22 | 9.9% | 1.2% | 6.8% | 0.8% | 25.35 | 0.31 | 180 |
| 23 | 10.2% | 1.3% | 7.0% | 0.9% | 26.48 | 0.41 | 240 |
| 24 | 0.0% | 0.0% | 0.0% | 0.0% | 19.51 | 0.23 | 0 |
| 2nd. Set | | | | | | $N_2$ | Pressure (mtorr) |
| 5 | 16.2% | 1.3% | 11.4% | 1.0% | 22.90 | 0.38 | 10 |
| 6 | 14.9% | 1.4% | 10.5% | 1.0% | 22.08 | 0.41 | 15 |
| 7 | 10.6% | 1.7% | 7.3% | 1.2% | 21.84 | 0.65 | 30 |
| 8 | 6.6% | 1.5% | 4.5% | 1.0% | 22.38 | 0.47 | 60 |

Environmental Effect

Figure 7A:
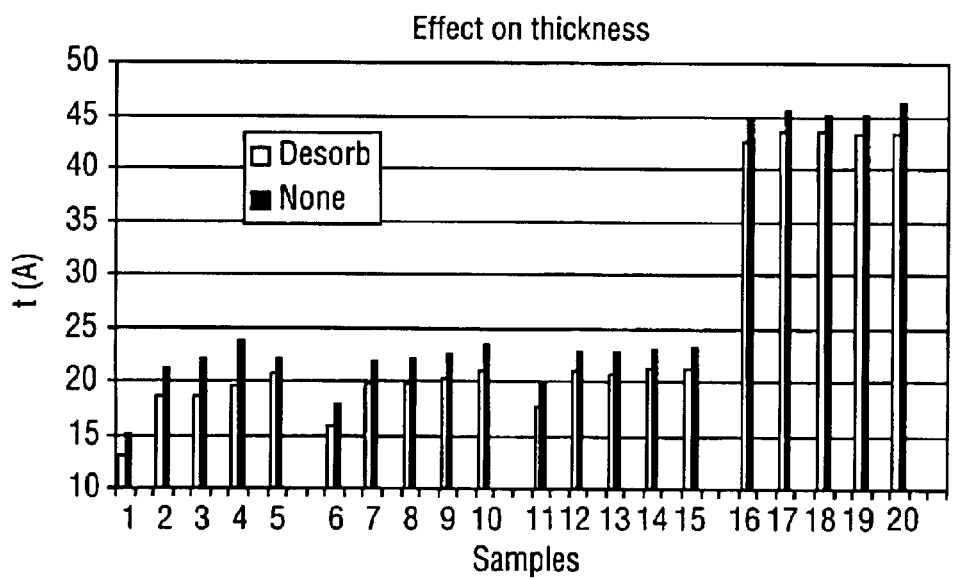
FIGS. 7a–c illustrate the effects of using a desorber to pre-treat the wafers prior to measurement.
Figure 7B:
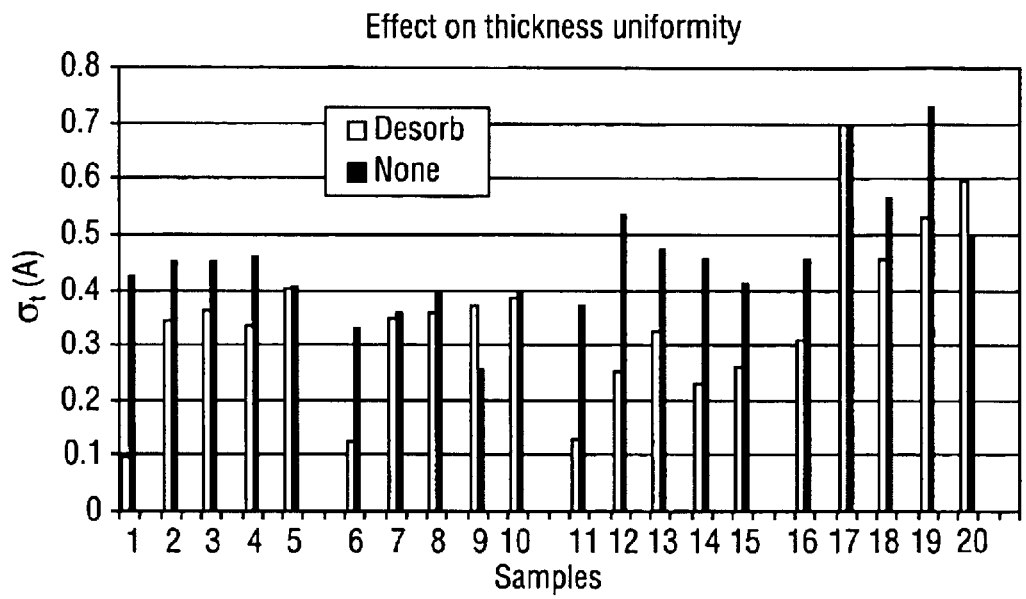
Figure 7C:
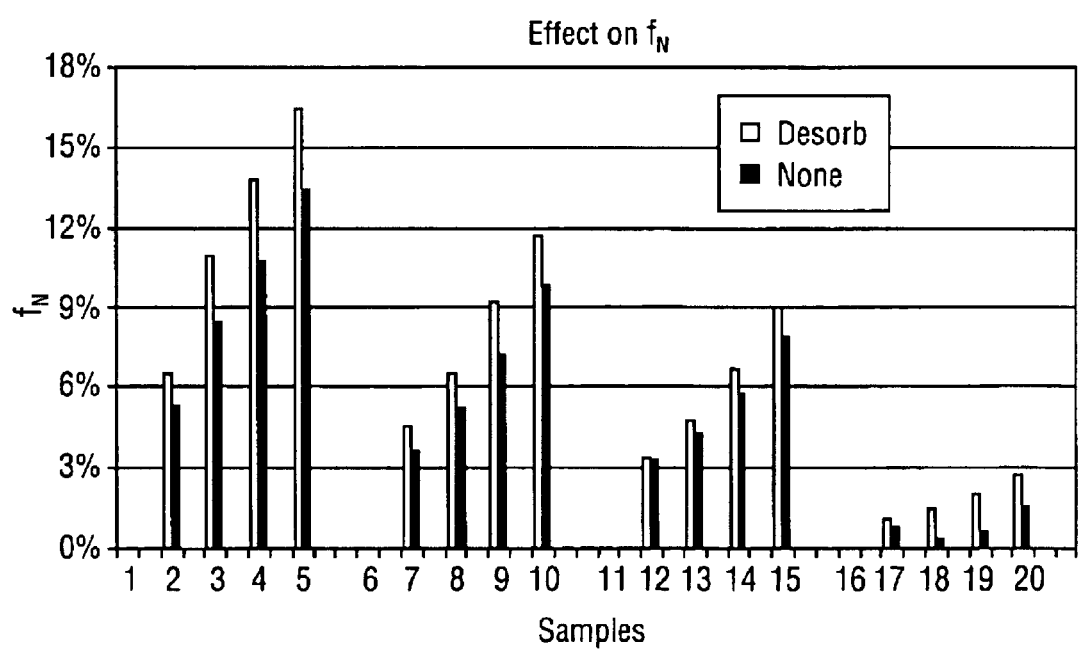

A side-by-side comparison of standard Opti-Probe results to Opti-Probe desorber results on all four subsets in the 3rd box was done. FIG. 7 illustrates the effects of environmental film on samples in the following aspects of a) thickness (mean thickness of each 21-pt. linescan), b) thickness uniformity (one sigma of each 21-pt. linescan), and c) nitrogen content (mean concentration of each 21-pt. linescan).

The increase of nitrogen content accommodating with decrease of film thickness was observed after desorbing each samples prior to standard OP measurements. Without desorbing samples prior to measurements, exiting of environmental film effectively dilutes nitrogen concentration. In the other word, the true nitrogen content can be determined using a desorber.

Process Dependency

Figure 8:
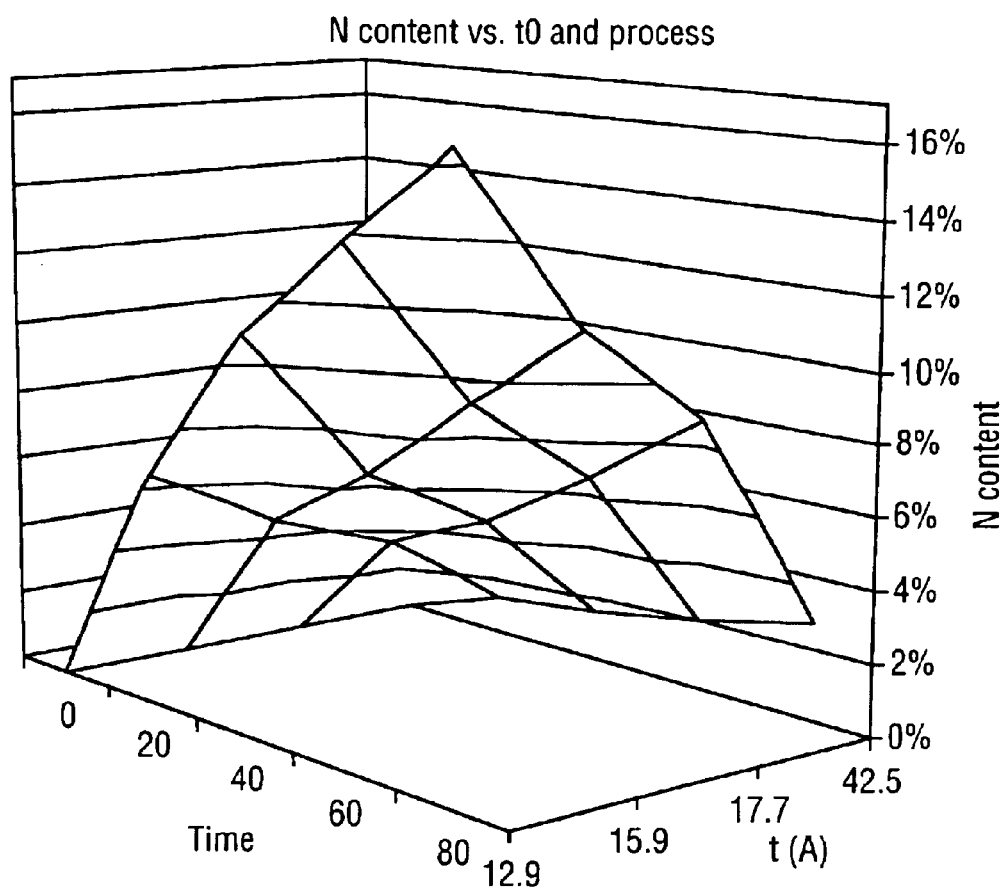
FIG. 8 is a graph correlating nitrogen content with process time and film thickness.

In the process, the nitrogen content can be varied by numerous process parameters as well as initial thin oxide thickness. Table 8 lists the initial mean wafer thickness, changes in one process parameter and mean nitrogen content per wafer of another wafer set. A process dependency of nitrogen content has been illustrated in FIG. 8, which is within process expectation.

TABLE 8

Average thickness and N content per wafer after desorbing

| | | Time (s) | | | | |
|---|---|---|---|---|---|---|
| | | 0 | 20 | 40 | 60 | 80 |
| Subset | Mean_$t_0$ (A) | | | Mean_$f_N$ | | |
| 1 | 12.9 | 0.0% | 6.5% | 10.9% | 13.8% | 16.5% |
| 2 | 15.9 | 0.0% | 4.6% | 6.6% | 9.3% | 11.7% |
| 3 | 17.7 | 0.0% | 3.4% | 4.7% | 6.6% | 8.9% |
| 4 | 42.5 | 0.0% | 1.1% | 1.4% | 2.0% | 2.7% |

Marathon Test

Figure 9A:
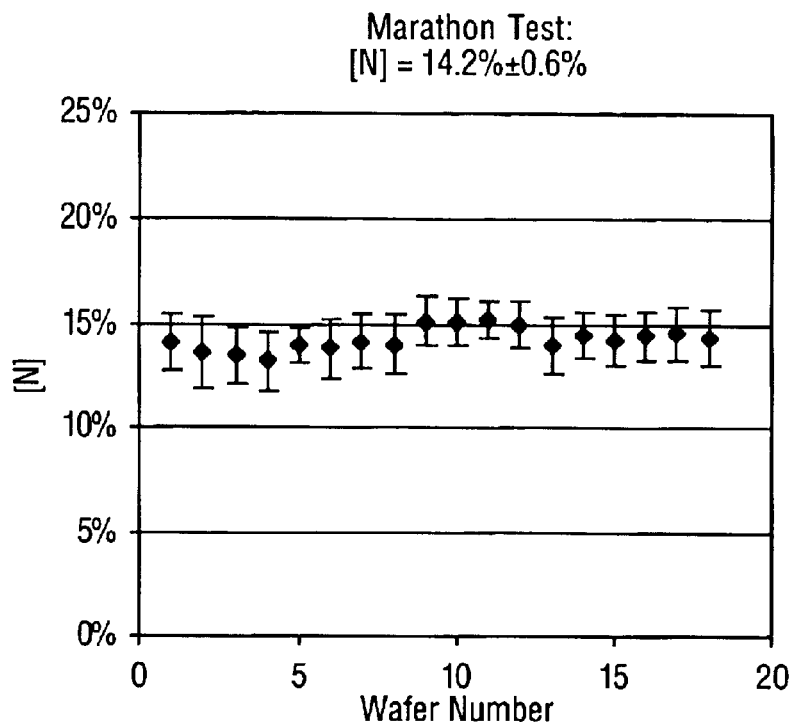
FIG. 9 is a graph representing marathon testing.
Figure 9B:
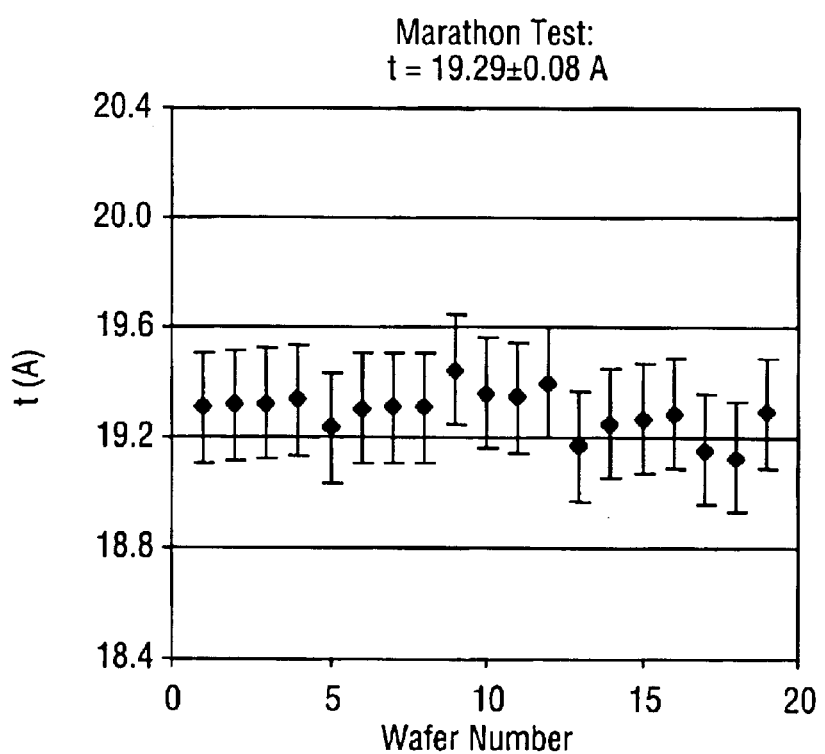

Eighteen samples under the same process condition were selected from various boxes. The nitrogen content as well as film thickness were determined using the AE/BB method on an Opti-Probe. The test was run repeatedly over many days. One sigma of 0.6% in wafer mean nitrogen content, and 0.08 A in wafer mean thickness were obtained as presented in FIG. 9. The error bars represent ± one sigma of each 21-pt line scan across each wafer.

A Parallel Study on a Thermal Wave Device (Therma-Probe-TP)

Figure 10A:
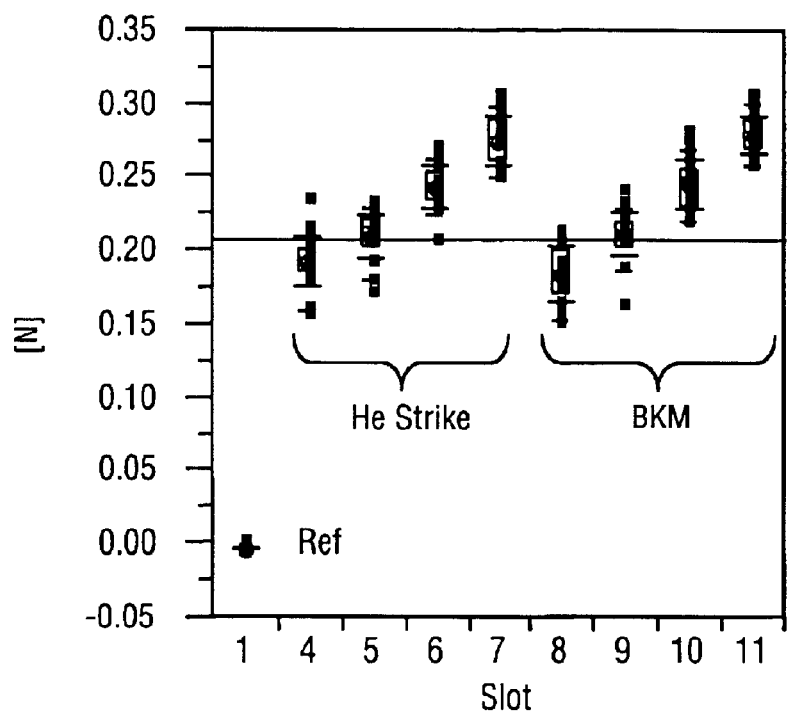
FIGS. 10a and 10b are graphs comparing the sensitivity of measurements made with the ellipsometer/broadband combination and the thermal wave technique.
Figure 10B:
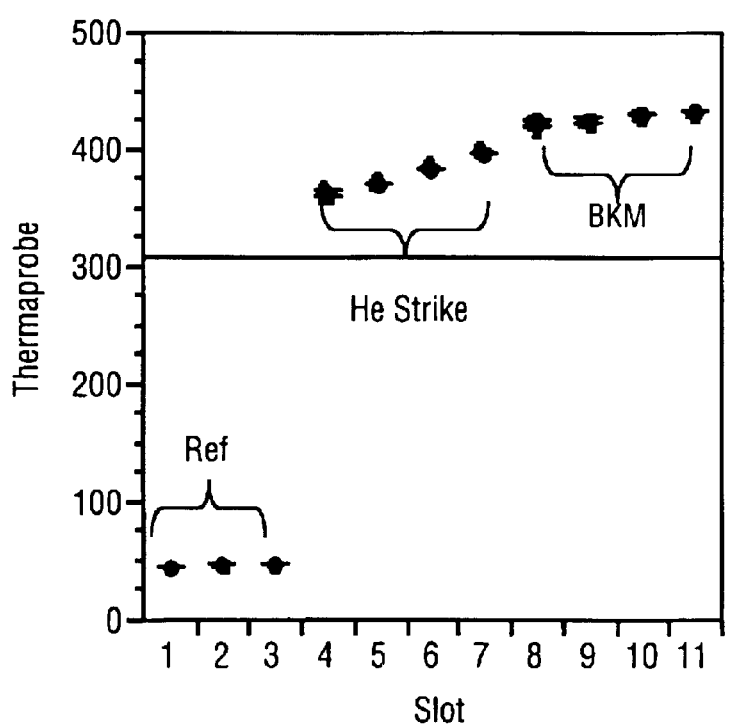

Under the decouple plasma nitridation process, different interface states between thin nitrided oxide and the Si-substrate were generated. FIGS. 10a and 10b shows that i) OP has sensitivity only to few process parameters leading to change in nitrogen content (i.e., process time, gas flow rate, etc.); ii) TP has extremely high sensitivity to any process parameters resulting in variation of surface states of Si-substrate. For this reason, the Therma-Probe cannot provide accurate nitrogen concentration data without calibration.

Figure 11A:
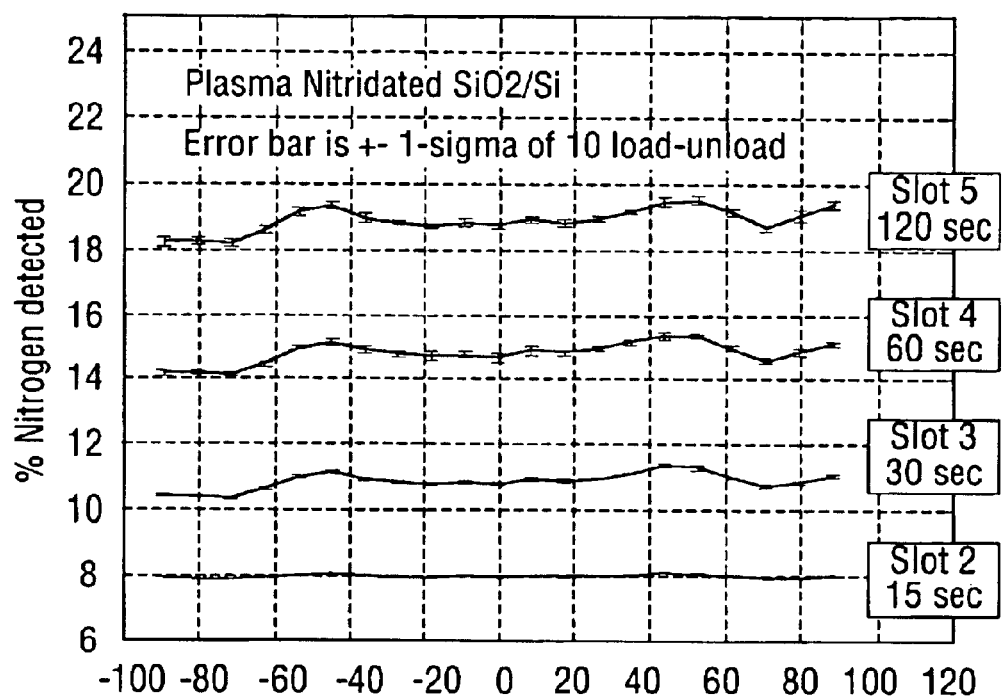
FIGS. 11a–c illustrates the use of an ellipsometer/broadband technique to calibrate a thermal wave measurement.
Figure 11B:
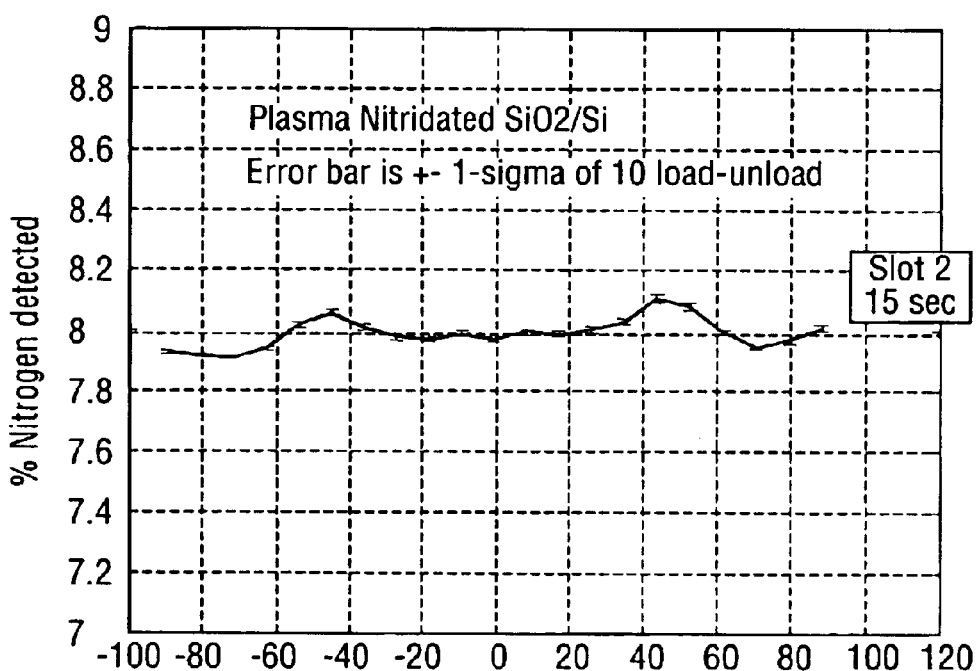
Figure 11C:
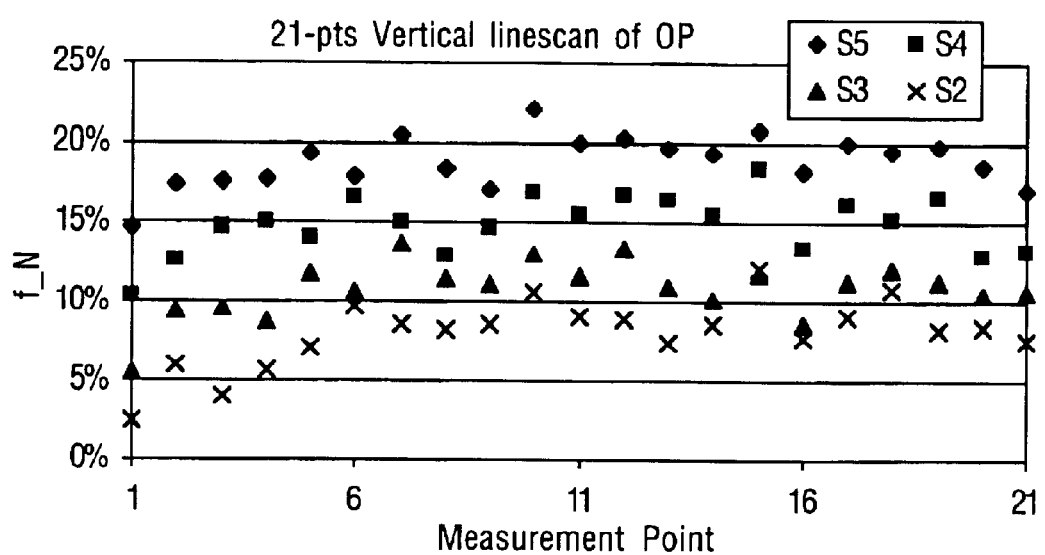

In this study, the nitrogen content at each wafer center determined on the Opti-Probe was applied to correlate Therma-Probe signal to nitrogen concentration as shown in FIG. 11. FIGS. 11a and b represents line scans across the wafer for the nitrided SiO2/Si wafers. The N concentration is calibrated using results from an Opti-Probe as shown in FIG. 11c.

A repeatability study on these wafers performed on a TP are also illustrated in FIG. 11, where error bars represents ± one sigma of 10-time load/unload per site of a 21-pt line scans across each wafer. The plots in FIG. 11 demonstrate that the thermal wave technique provides a twenty fold of improvement in one sigma in comparison to OP results in FIGS. 4 and 5.

Overall, it should be apparent that the precision of the measurements obtained from the Therma-Probe is far higher than with the Opti-Probe. However, since the Therma-Probe signal is effected by process parameters, it will not provide an accurate value for nitride concentration without prior calibration using an Opti-Probe. As noted above, the Opti-Probe provides a very accurate value for nitrogen concentration because of the large amount of data it collects and the data fitting algorithms which it uses. An Opti-Probe could also achieve a level of precision similar to the Therma-Probe, however, the measurements would take a very long time, as much as a hundred times longer than the Therma-Probe.

Given the very high precision which can be obtained by the Therma-Probe in a very short time, these type of measurements are ideal for fast monitoring of the nitration process. More specifically, the tool could be used to monitor wafers in quickly, in real time, immediately after the nitration process. Variations in the thermal wave signal would indicate either a change in the nitrogen level or a variation in the process parameters, either of which could indicate a problem with the fabrication of the wafer.

As for implantation samples, the Therma-Probe signal can be washed out after a thorough annealing process. More specifically, after annealing the wafer, the thermal wave signal will be the same for a given sample (i.e. silicon with a layer of silicon dioxide of known thickness) regardless of the level of nitrogen in the sample. Thus, a thermal wave tool will be a useful tool for monitoring the annealing process after decoupling from plasma nitridation process.

Summary of Experiments

With trends of shrinking critical dimension, the thinner gate dielectric material with better electronic performance than traditional SiO2 has been required. With years of developments, nitrided oxide film has been selected as the best SiO2 replacement for the gate dielectric material for the next generation devices. For either process improvement or process control, both process equipment suppliers and IC manufactures have been searching for a reliable, fast, or a production available metrology. Currently there are only few available techniques used in surface science, i.e., SIMS, XPS, NRA, which is either slow or destructive and are very expensive.

Thickness, nitrogen content and interface states are three key parameters to quality of the process. A combination of Opti-Probe and Therma-Probe can provide a solution for both equipment makers and IC manufactures. The concept of this new method has been verified on various samples processed under either RPN or DPN process in both reliability and stability.

Thermal/Plasma Wave Measurements

Figure 12:
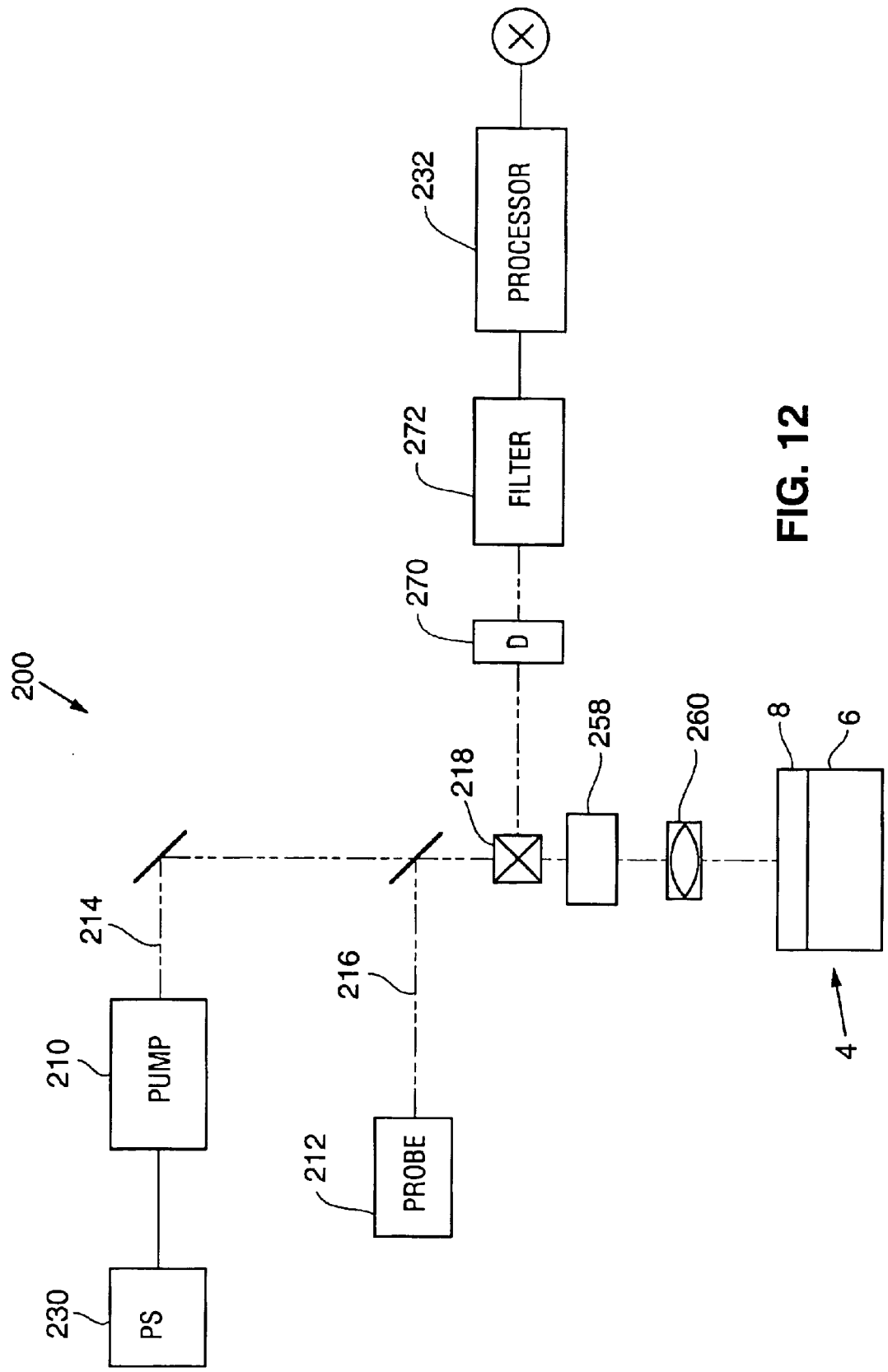
FIG. 12 is an illustration of a thermal/plasma wave metrology tool.

Referring to FIG. 12, a device suitable for measuring thermal and/or plasma waves in semiconductors is shown. Only the basic elements are illustrated herein. Further details about such a device can found in some of the above cited references as well as U.S. Pat. No. 5,978,074 incorporated herein by reference.

Apparatus 200 includes a pump laser 210 for exciting the sample and a probe laser 212 for monitoring the sample. Gas, solid state or semiconductor lasers can be used. As described in the assignees earlier patents, other means for exciting the sample can include different sources of electromagnetic radiation or particle beams such as from an electron gun.

In the preferred embodiment, semiconductor lasers are selected for both the pump and probe lasers due to their reliability and long life. For example, pump laser 210 generates a near infrared output beam 214 at 790 nm while probe laser 212 generates a visible output beam 216 at 670 nm. The outputs of the two lasers are linearly polarized. The beams are combined with a dichroic mirror 218. It is also possible to use two lasers with similar wavelengths and rely on polarization discrimination for beam combining and splitting.

Pump laser 210 is connected to a power supply 230 which is under the control of a processor 232. The output beam of laser 210 is intensity modulated through the output of power supply 230. The modulation frequency typically has a range anywhere from 10 KHz to 100 MHz.

After the beams 214 and 216 are combined, they pass through a quarter-wave plate 258 for rotating the polarization of the beams by 45 degrees. The beams are directed down to the sample 12 through a microscope objective 260. Objective 260 has a high n.a., on the order of 0.9, and is capable of focusing the beam to a spot size on the order of a few microns and preferably close to one micron in diameter. The spacing between the objective and the sample is controlled by an autofocus system (not shown).

The returning reflected beams 214 and 216 pass through the quarter-wave plate 258 a second time, resulting in another 45 degree polarization rotation. This second rotation allows the beams to be reflected by the beam splitter 258 towards detector 270. Prior to reaching the detector, the beams strike wavelength selective filter 272 which removes the pump beam light 214 allowing only the probe beam light 216 to be measured by the detector.

Detector 270 provides an output signal which is proportional to the power of the reflected probe beam 216. Detector 270 is arranged to be underfilled so that its output can be insensitive to any changes in beam diameter or position. In the preferred embodiment, detector 270 is a quad cell generating four separate outputs. When used to measure reflected beam power, the output of all four quadrants are summed. When the subject apparatus is operated to measure beam deflection, the output of one adjacent pair of quadrants is summed and subtracted from the sum of the remaining pair of quadrants. This latter beam deflection measurement is discussed in greater detail in the above cited patents.

The output of the photodetector 270 is passed through a low pass filter 272 before reaching processor 232. One function of filter 272 is to pass a signal to the processor 232 proportional to the DC power of the reflected probe. Another function of filter 272 is to isolate the changes in power of the reflected probe beam which are synchronous with the pump beam modulation frequency. In the preferred embodiment, the filter 272 includes a lock-in detector for monitoring the magnitude and phase of the periodic reflectivity signal. Because the modulation frequency of pump laser can be so high, it is preferable to provide an initial heterodyne downmixing stage for reducing the frequency of detection. The resulting signals are filtered and demodulated. The outputs of demodulation stage are the "in-phase" and "quadrature" signals typical of a lock-in amplifier. The in-phase and quadrature signals can be used by processor 232 to calculate the magnitude and the phase of the modulated optical reflectivity signal.

As an alternative to using an electronic heterodyne downmixing system, it is also possible to reduce the frequency of detection using an optical heterodyne approach. Such an optical approach is disclosed in U.S. Pat. No. 5,408,327, incorporated herein by reference. In the latter system, both of the laser beams are modulated but at slightly different frequencies. Both beams generate thermal and plasma waves at their respective modulation frequencies. The beam from one laser picks up an intensity modulation upon reflection due to the modulated optical reflectivity induced in the sample by the other beam. The MOR signal picked up upon reflection "mixes" with the inherent modulation of the beam, creating additional modulations in the beam at both the sum and difference frequency. This process is analogous to electrical heterodyning. The difference or "beat" frequency is much lower than either of the initial beam modulation frequencies and can therefore be detected by a low frequency lock-in amplifier.

To insure proper repeatability of the measurements, the signals must be normalized in the processor. Accordingly, and as discussed in the above identified patents, in the preferred embodiment, a variety of reference detectors would be provided, the outputs of which are used to normalize the output of detector 270. Other optical elements, such as filters, collimators, shutters and steering optics would be included, all of which are all well known to those skilled in the art.)

It has been well established that such a system can be used to evaluate the level of ion implantation in a semiconductor. Ion implantation creates damage in the crystalline structure which impedes the flow of the thermal and plasma waves which can be measured.

It has also been known to use such equipment to measure the thickness of thin metal films. In addition, such equipment has been used to monitor the surface states of a material. More specifically, and as recited in U.S. Pat. No. 4,750,822, incorporated herein by reference, variations in the thermal wave signal over time can be used to evaluate defect surface states. It is believed that the sensitivity of the thermal wave signal to nitrogen concentration is in some way related to the surface states existing between the silicon and the gate oxide. It is also believed that until now, this type of device has not been used to evaluate the concentration of nitrogen in gate dielectrics. Further, in the proposed method, information about nitrogen levels is obtained from an immediate measurement as does not require an evaluation of the decay of the signal as described in U.S. Pat. No. 4,750,822. It should be noted that a decay in the signal has also been observed when measuring nitrided oxide and it is believed that additional information about the sample structure could be obtained from a decay analysis of the type described in U.S. Pat. No. 4,740,822

As noted above, a thermal wave device is very sensitive to nitrogen levels and process parameters. Thus, the output thereof can be used to monitor variations in these parameters. The device could be operated without calibration if only process variations were of interest. In such a case, any change in signal would be used an indicator that some variable in the fabrication step had changed. If more accurate information is desired, some samples could be measured with another tool, such as the ellipsometer/broadband technique disclosed above and the data obtained could be used to calibrate the thermal wave data.

In order to improve accuracy, it may be desirable to equip a single tool with the capability of making both ellipsometer/broadband measurements as well as thermal/plasma wave measurements. Providing multiple measurement tools on a single platform allows the probe beams to easily measure at the same spot on the wafer without moving the wafer. In addition, a single tool has a smaller footprint and therefore takes up less floor space in the semiconductor fabrication facility. By combining technologies in a single tool, costs can be reduced by eliminating duplicate subsystems such as wafer handlers and computers. Finally, the combination can simplify and streamline decision making since the information from the multiple measurement modalities can be coordinated instead of producing conflicting results as in the prior art when two separate devices might be used.

Figure 13:
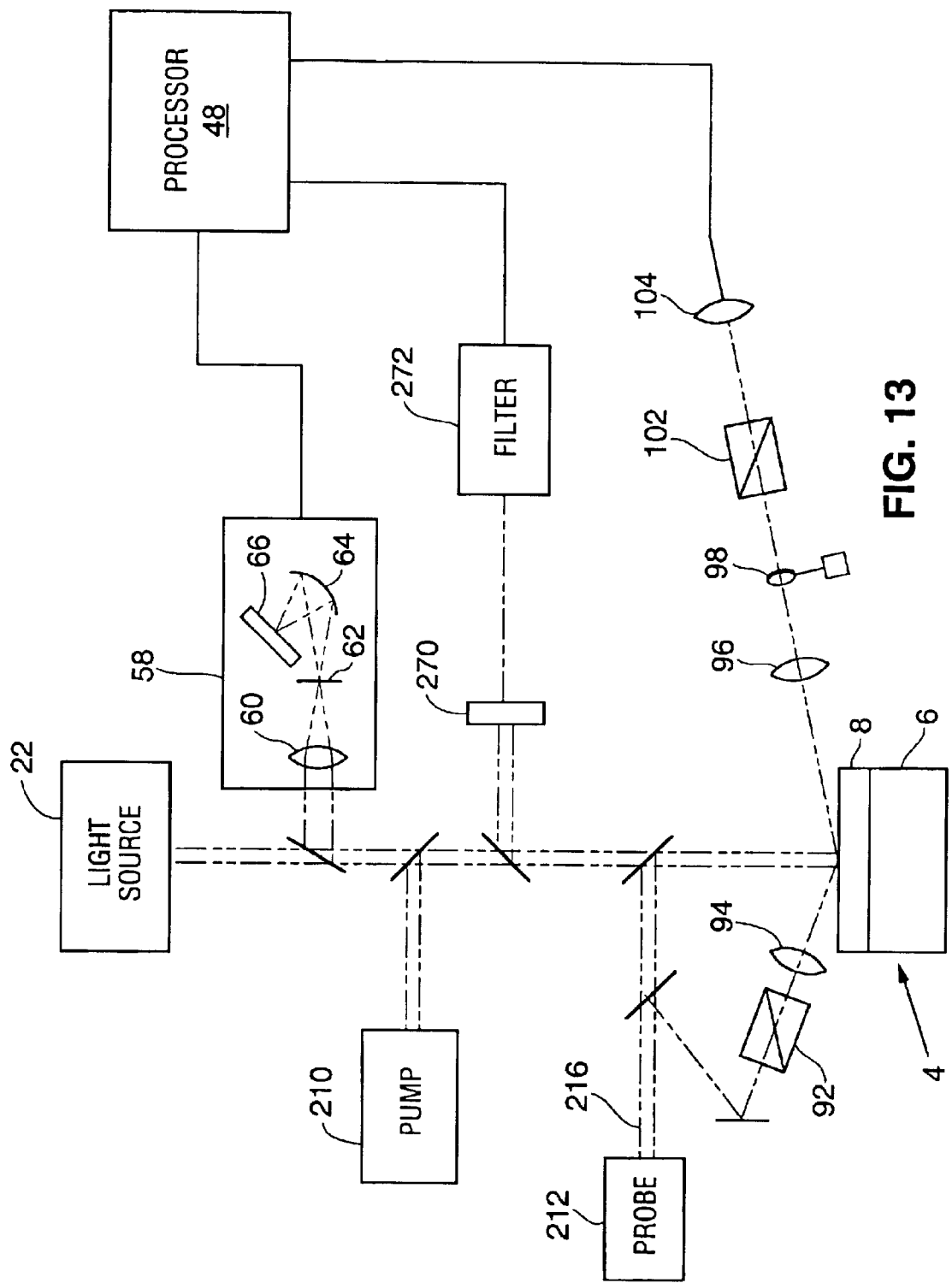
FIG. 13 illustrates one form of a combination tool including a single wavelength ellipsometer, a broadband spectrometer and a thermal/plasma wave tool.

A basic form of such a tool is illustrated in FIG. 13. As will be seen, elements from the ellipsometer/broadband device of FIG. 1 and the thermal/plasma wave device of FIG. 12 have been combined (with like reference numbers being used). Some elements have been omitted for clarity and only the main elements are shown. Since the operation of the measurement tools are the same, the will not be described again.

As can be seen in FIG. 13, the pump and probe light sources are provided for the thermal wave measurement. In this case, in might be possible to use the a single probe light source for both the thermal wave system and the narrow band ellipsometer and thus only one is shown. Specifically, probe 212 provides a beam 216 which is measured by detector 270 to obtain the thermal wave signal. In addition, a portion of the probe beam 216 can be redirected to strike the sample off-axis so that its polarization information can be derived with the compensator 98, analyzer 102 and detector 104. Depending upon the particular requirements, two different lasers could be used to generate two different probe beams (i.e. a semiconductor laser diode for the thermal wave probe and a helium-neon laser for the stable wavelength ellipsometer probe).

FIG. 13 also illustrates a broadband spectrophotometer, including light source 22 and the spectrometer detector 58. The subject tool could also be configured to perform broadband ellipsometry, beam profile reflectometry or beam profile ellipsometry as discussed with reference to FIG. 1.

The output from the various detectors are combined in the processor in a manner to reduce ambiguities in the measurements. This combination can include various fitting algorithms. Alternatively, the ellipsometer/broadband measurement can be used to calibrate the thermal/plasma wave measurement, allowing the thermal/plasma wave measurement to be used on subsequent samples.

As noted above, there are many different thermal/plasma wave measurement techniques besides the measurement of modulated optical reflectivity. These devices are described in the above-cited patents and include measurement of the angular deviations of the probe beam as well as interferometric techniques. In addition, there are some related techniques, which include monitoring stress pulses or acoustic waves, that could also be applied to the subject invention. All of these techniques have in common the use of a pulsed pump beam to excite the sample and a separate probe beam for investigating the effects of the pump. Those devices are also with the broad scope of the subject invention. Such systems are described in U.S. Pat. Nos. 4,710,030 and 6,081,330, also incorporated by reference.

While the subject invention has been described with reference to a preferred embodiment, various changes and modifications could be made therein, by one skilled in the art, without varying from the scope and spirit of the subject invention as defined by the appended claims.

We claim:

1. A method for evaluating the nitrogen content in a thin film dielectric layer formed on a sample comprising the steps of:

periodically exciting a region of the surface of the sample;

monitoring the effects of the periodic excitation with an optical probe and generating output signals in response thereto;

evaluating the nitrogen content of the thin film dielectric layer based on the output signals.

2. A method as recited in claim 1, wherein the optical probe monitors the modulated optical reflectivity of the sample induced by the periodic excitation.

3. A method as recited in claim 1, wherein said optical probe monitors deformations of the surface of the sample induced by the periodic excitation.

4. A method as recited in claim 1, wherein the optical probe is defined by a probe beam and wherein periodic angular deflections of probe beam are monitored.

5. A method as recited in claim 1, wherein the evaluation includes comparing the output signals to a predetermined value to facilitate fabrication process control.

6. A method as recited in claim 1, further including a calibrating step wherein the results of the evaluation are compared with the results of a separate and independent measurement.

7. A method as recited in claim 6, wherein said separate and independent measurement includes the steps of:

measuring the sample using an off-axis ellipsometer which includes a stable narrow band wavelength source and generating first output signals;

measuring the response of the sample to reflected light from a polychromatic source by analyzing either the change polarization state of the light or the magnitude of the light induced by reflection off the surface of the sample and generating a plurality of second output signals corresponding to different wavelengths; and evaluating the nitrogen content of the thin film dielectric layer based on a combination of the first and second output signals.

8. A method for evaluating the nitrogen content in a thin film dielectric layer formed on a sample comprising the steps of:

directing an intensity modulated pump laser beam to a spot on the surface of the sample for periodically exciting the sample;

directing a probe laser beam to a spot on the surface of the sample within a region that has been periodically excited and is reflected therefrom;

monitoring the reflected probe beam to determine the effects of the periodic excitation on the sample and generating output signals in response thereto; and filtering the output signals to provide a measure of the magnitude or phase of the modulated changes in the sample and using the result to evaluate the nitrogen content in the thin film dielectric layer.

9. A method as recited in claim 8, wherein change in power of the reflected probe beam are monitored to determine the modulated optical reflectivity of the sample induced by the periodic excitation.

10. A method for evaluating the nitrogen content in a thin film dielectric layer formed on a sample comprising the steps of:

directing an intensity modulated pump laser beam to a spot on the surface of the sample for periodically exciting the sample;

directing a probe laser beam to a spot on the surface of the sample within a region that has been periodically excited and is reflected therefrom;

monitoring the power of the reflected probe beam to determine the effects of the periodic excitation on the sample and generating output signals in response thereto;

filtering the output signals to provide a measure of the magnitude or phase of the modulated optical reflectivity of the sample; and comparing the filtered output signals to a predetermined value to determine whether the expected concentration of nitrogen is present in the thin film dielectric layer.

11. A method of evaluating the annealing of a wafer having a thin oxide film dielectric formed thereon, said thin film dielectric having a nitrogen concentration, comprising the steps of:

periodically exciting a region of the surface of the sample;

monitoring the effects of the periodic excitation with an optical probe and generating output signals in response thereto; and evaluating the extent of the annealing of the wafer based on the output signals.

12. A method of fabricating a wafer comprising the steps of:

forming a thin, oxide dielectric layer over a substrate;
   adding nitrogen to the oxide dielectric layer;
   annealing the wafer;
   periodically exciting a region of the wafer;
   monitoring the effects of the periodic excitation with an optical probe and generating output signals in response thereto; and
   evaluating the extent of the annealing of the wafer based on the output signals.

* * * * *